US006287565B1

(12) United States Patent
Zimmerman et al.

(10) Patent No.: US 6,287,565 B1
(45) Date of Patent: *Sep. 11, 2001

(54) MODIFIED HGP-30 HETEROCONJUGATES, COMPOSITIONS AND METHODS OF USE

(75) Inventors: Daniel H. Zimmerman, Bethesda; Prem S. Sarin, Gaithersburg, both of MD (US)

(73) Assignee: Cel-Sci Corporation, Vienna, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/594,845

(22) Filed: Jun. 15, 2000

Related U.S. Application Data

(63) Continuation of application No. 08/695,304, filed on Aug. 8, 1996, now Pat. No. 6,103,239.

(51) Int. Cl.$^7$ ..................................................... A61K 38/00

(52) U.S. Cl. ................................. 424/188.1; 424/185.1; 424/186.1; 424/196.11; 424/187.1; 514/12; 514/13; 530/324; 530/327; 530/826

(58) Field of Search ............................. 424/185.1, 186.1, 424/188.1, 196.11, 187.1; 514/12, 13; 530/324, 327, 826

(56) References Cited

U.S. PATENT DOCUMENTS

| | | |
|---|---|---|
| 4,983,387 | 1/1991 | Goldstein et al. . |
| 5,449,761 * | 9/1995 | Belinka, Jr. et al. .................. 534/10 |
| 5,589,384 * | 12/1996 | Lipscombe et al. ............. 435/252.33 |
| 5,620,956 * | 4/1997 | Clayberger et al. .................... 514/14 |
| 6,100,377 * | 8/2000 | Greene ................................. 530/317 |
| 6,103,239 * | 8/2000 | Zimmerman et al. ............ 424/188.1 |

FOREIGN PATENT DOCUMENTS

| | | |
|---|---|---|
| 0231728 * | 8/1987 | (EP) . |
| 0620010 | 10/1994 | (EP) . |
| 89/12458 | 12/1989 | (WO) . |
| 8912458 | 12/1989 | (WO) . |
| 9738011 | 10/1997 | (WO) . |

OTHER PUBLICATIONS

Zimmerman, et al., Immunization with Peptide Heteroconjugates Primes . . . , Vaccine Research, vol. 5, No. 2, 1996, pp. 103–118.
Uger, et al., Creating CTL Targets with Epitope–Linked . . . , J. Immunology, 1998, 160:1598–1605.
Uger, et al., Covalent Linkage to $\beta_2$–Microglobulin Enhances . . . , J. Immunology, 1999, 162:6024.
White, et al., Soluble Class I MHC with $\beta_2$–Microglobulin Covalently . . . , J. Immunology, 1999, 162:2671–2676.
Reineke, et al., A synthetic mimic of a discontinuous binding site on . . . , Nature Biotechnology, vol. 17, Mar. 1999, pp. 271–275.
Heegaard, et al., A Stem Peptide Carrier for the Immunogenic . . . , 1998, Chapter 32, Mayflower Scientific, Birmingham, England.
Finkelman, et al., Ann Rev Immunol 8:303 (1990).
Snapper, et al., Science 236:944 (1987.
Salgame, et al., Science 254:279 (1991).
Romagnani, Immunol Today 13:379 (1992).
Bretsher, et al., Science 257:539 (1992).
Cox, et al., Immunol Today 13:445 (1992).
Mosman, et al., Ann Rev Immunol 7:145 (1989).
Taylor–Robinson, et al., Science 260:1931 (1993).
Khalife, et al., AIDS Res and Hu Retro 4:3 (1988).
Wicker, et al., Eur. J. Immunol. 14:442 (1984).
Zimmerman, et al., Vaccine Res. 5:91 (1996).
Zimmerman, et al., Vaccine Res. 5:103 (1996).
Kawano, et al., J. Immunol. 152:4948 (1994).
Lundgren, et al., Eur. J. Immunol. 19:1311 (1989).
Bird, et al., Immunol. 69:355 (1990).
Hadjipetrou–Kourounakis, et al., Scan. J. Immunol. 19:219 (1984).
Kenney, et al., J. Immunol. Meth. 121:157 (1989).
van de Wihgert, et al., Infect. Immun. 59:2750 (1991).
Golding, et al., Am. J. Trop. Med. Hyg. 50 (4) suppl:33 (1994).
Lachman, et al., AIDS Res. Hu. Retroviruses 11 (8):921 (1995).
Bui, et al., J. AIDS 7:799 (1994).
Sercarz, et al., Immunol. Today 12:111 (1991).
Yowell, et al., Nature, 279:70 (1979).
Naylor, et al., Mono. Viro. 18:74 (1990).
Coates, et al., Nature 326:549 (1987).
Wahren, et al., J. AIDS 4:448 (1989).
Mosier, et al., Proc. Nat. Acad. Sci. 90:2443 (1993).
Parren, et al., AIDS 9 (6) :F1–6 (1995).
Sarin, et al., Science 232:1135 (1986).
Naylor, et al., Proc. Nat. Acad. Sci. 84:2951 (1987).
Gazzard, et al., Vaccine Res. 1:129 (1992).
Sarin, et al., Vaccine Res. 3:49 (1994).
Kahn, AIDS Res. Hu. Retroviruses 8:1321 (1992).
Naylor, et al., Int. J. Immunopharm 13 (Suppl) :117 (1991).
Sarin, et al., Cell Molec. Biol. 41:401 (1995).
Kahn, et al., Abstract 13, International AIDS Conference, Vancouver, Canada, Jul. 1996.

(List continued on next page.)

*Primary Examiner*—Jeffrey Stucker
(74) *Attorney, Agent, or Firm*—Sherman & Shalloway

(57) ABSTRACT

A heteroconjugate is formed by linking a T cell binding ligand (TCBL) such as Peptide J of β-2 microglobulin to a modified HGP-30 antigenic peptide fragment of p17 gag peptide, such as, for example

A T L  Y S V  H Q R  I D V  K D T    (SEQ ID NO: 5)

K E A  L E K  I E E  E Q N  K S

The heteroconjugate is effective in eliciting a THI directed immune response and provides a vaccine composition for treating or preventing AIDS.

10 Claims, No Drawings

OTHER PUBLICATIONS

Talmadge, et al., Clin. Immunol., Meeting, New Orleans, LA, Jun. 1996.
Willer, et al., Biomed. & Pharmacol. 46:359 (1992).
McDougal, et al., J. Clin. Invest. 80:316 (1987).
Jiang, et al., J. AIDS 5:382 (1992).
Broliden, et al., Clin. Expt. Immunol. 76:216 (1989).
Ljunggren, et al., J. Immunol. Meth 104:7 (1987).
Ljunggren, et al., Clin. Exp. Immunol. 73:343 (1987).
Shakib, F., Ed., "The Human IgG Subclasses: Molecular Analysis of Structure, Function, and Regulation" Jeffries, et al, Chapt. 6, p. 93; Pound, et al., Chapter 7, p. 111; Weiner, Chapter 8, p. 135 (1990).
Rook, et al., J. Immunol 138:1064 (1987).
Mosier, et al., Science 251:791 (1991).
Mosier, et al., AIDS Res. Hu. Retro., 8:1387 (1992).
Papsidero et al., J. Virol. 63:267 (1989).
Boucher, et al., Clin. Lab. Anal. 4:43 (1990).
K. Taniguchi, et al., Slight difference in primary amino acid sequence . . . ,.
Arch Virol (1998) 143:881–890.
Sarin, et al., Vaccine Research, vol. 3: 49–57, 1994.
Klasse, et al., J. of Infectious Diseases, vol. 156: 1026–1029, 1987.

* cited by examiner

MODIFIED HGP-30 HETEROCONJUGATES, COMPOSITIONS AND METHODS OF USE

CROSS-REFERENCE TO RELATED APPLICATIONS

This application is a continuation of application Ser. No. 08/695,304, filed Aug. 8, 1996, now U.S. Pat. No. 6,103,239.

BACKGROUND OF THE INVENTION (1) Field of the Invention

This invention relates to heterofunctional peptide conjugates derived, in part, from the p17 gag protein of human immunodeficiency virus (HIV) which is the causative organism of the disease known as Acquired Immune Deficiency Syndrome (AIDS). More particularly, the invention relates to the use of certain p17 peptide fragments and analogues as a component of a heterofunctional conjugate with a T cell binding ligand (TCBL) and to an AIDS vaccine based on such heterofunctional conjugate and to the use of the resulting AIDS vaccine compositions in a method for treating or preventing AIDS which method is based on the discovery that the heterofunctional peptide conjugates are capable of eliciting TH1 associated antibodies and other aspects of a TH1 cellular immune response.

(2) Discussion of the Prior Art

There has been extensive research over the past several years, first to identify the cause of AIDS and after the positive identification of the retroviruses generically referred to as HIV, as the causative organism, efforts have concentrated on more detailed analysis of the genetic makeup, molecular biology, pathogenesis, biochemistry, development of highly sensitive methods of detection of virus and antibodies and treatment protocols, and therapies. Extensive progress has been made in all of these areas yet much work needs to be done to effectively combat the spread of AIDS. An essential part of the approach for combatting the spread of the highly infectious HIV virus is the development of effective vaccines that stimulate the appropriate components of the immune system. In this regard, knowledge of the natural history of infection with HIV and the various immune responses and the clinical condition and the outcome may be useful in preparing effective vaccine preparations for either therapeutic or preventive means. In this regard accurate diagnosis of the stage of disease and the immune status with regard to HIV and the knowledge that certain means are available may encourage infected patients to alter or modify their lifestyles in such manner as to reduce the risk of spreading the virus.

Additionally, identification of protective antibodies based on epitope recognition can offer a more effective mechanism for staging and/or diagnosing the AIDS or pre-AIDS disease. Such staging and early diagnosis of seropositive individuals may then allow for vaccinations to provide the appropriate protective immune responses for treating the seropositive individual.

For many infectious diseases it is now recognized that the presence or absence of antibody is not as critical in the satisfactory clearance of the agent and disease resolution as much as it is the class or subclass of antibody, other immune system activities such as cytotoxic T lymphocytes and the particular antigens of the agent being recognized. For example, resolution of intracellular infections, such as tuberculosis, require activation of delayed-type hypersensitivity (DTH) and helper T cell activities, properties of CD4+ T cells (Finkelman et al. 1990, Ann Rev Immunol 8:303). CD4+ T helper cells have been delineated into TH1 and TH2 subsets in the mouse based on the cytokines produced and other activities which are promoted or associated with the T cell (Snapper et al 1987, Science 236:944; Salgame et al 1991, Science 254:279; Romagnani 1992, Immunol Today 13:379). In the mouse TH1 cells promote DTH, produce IL-2, interferon-γ and promote IgG2a synthesis and inhibit TH2 responses, whereas TH2 cells produce IL-4, IL-10, promote B cell growth and differentiation leading to IgG1 and IgE production and inhibit TH1 responses (Bretsher et al 1992, Science 257:539). CD8+ cytotoxic T cell responses are also associated with TH1 responses (Cox et al.1992 Immunol Today 13:445). Based upon this information the nature of the T cell response generated by a specific immunization protocol can be evaluated by measurement of the specific lymphokine and/or antibodies produced (Finkelman et al. 1990, Annu Rev Immunol 8:303; Mosmann et al. 1989, Ann Rev Immunol 7:145). More recently it has been recognized that CD8+ cells responsible for CTL activity form a part of the cellular immune response mediated by TH1 cells (Taylor-Robinson et al. 1993, Science 260:1931).

HIV has several major classes of proteins referred to as the outer envelope structural group (env gp120 and p41), gag (or internal structural proteins p24, p17) and several nonstructural and regulatory genes and encoded proteins. Examination of the immune response and the disease state can be of assistance in designing new agents as vaccines. In one study, the response to HIV gag was polyisotypic (all/most classes or subclasses, IgM, IgG1, IgG3 and IgA) but antibodies to env were strikingly restricted to IgG1, (Khalife et al 1988, AIDS Res. and Hu. Retroviruses 4:3). The immune response to the nonstructural protein F (3'orf) also was restricted to IgM, IgA and IgG1 but not as much as the response to env and Khalife et al, ibid, further noted that IgG4 and IgE response which was gag restricted was found to be confined to the Hemophiliacs group.

Interestingly, in regard to man and HIV it is recognized that the disappearance of a particular subclass of antibodies (IgG3) to a conserved p17 protein molecule is most closely associated with disease progression. Antibodies to HIV of IgG1 and IgG2 subclasses are found in nearly all sera from HIV infected individuals at different stages of the disease. However, the presence of IgG3 is largely associated with gag proteins (p17, p24 and p55). Conversely almost all antibodies to the major viral surface proteins p41 and gp120 are of the IgG1 subclass and are present even in late stage disease (McDougal et al 1987 J. Clin, Invest 80:316–24).

The findings of McDougal et al ibid and also Jiang et al (J AIDS 1992, 5:382) are, in part, at odds with those of Broliden et al (1989 Clin. Expt. Immunol. 76: 216). Broliden ibid found IgG3 antibodies, predominantly against gag proteins at all stages of disease, and IgG1 which was against all HIV antigens declining in latter stages of the disease in contrast to McDougal et al ibid. Jiang et al ibid showed that anti p17 antibodies declined with disease progression and, in part, this was associated with antibodies to certain peptides of p17 including HGP-30. Broliden et al, ibid, refer to neutralizing antibody as being of the IgG3 subclass but conclude that no HIV neutralizing antibodies of IgG3 have been found. Broliden et al, ibid, in their study relates with HIV ADCC to IgG1 and not IgG3, (see also Ljunggren et al, 1987, 8, J.Immunol Meth 104:7; Clin Exp. Immunol, 1987, 73:343). Others suggest that ADCC is associated with IgG3. Often it is found that ADCC is associated with IgG3 ("The Human IgG Subclasses: Molecular Analysis of Structure, function and Regulation" Shakib, F. ed., Pergamon Press, 1990: Jeffries et al, Chapter 6, p.93; Pound et al, Chapter 7, p.111; Weiner, Chapter 8, p.135).

Rook et al (J. Immunol 1987, 138:1064) have shown that ADCC was associated with higher levels of antibodies to gag p24 than env. These workers did not examine antibodies to p17, various synthetic peptides of the proteins or the isotypes of the antibodies. Rook et al, ibid, also demonstrated higher levels of ADCC in asymptomatic HIV seropositive individuals than in AIDS patients.

The SCID Hu PBL mouse provides a very useful model that can be reconstituted with human cells and that can be infected with multiple strains of HIV (Mosier et al 1991, Science 251:791). This model allows for studying not only infection but also immunological intervention and control. Use of recombinant (r) gp160 (rgp160) for vaccination and demonstration of limited and short lived protection in the SCID model has been shown by Mosier et al (1993, Proc. Nat Acad. Sci 90:2443–2447). They showed the usefulness of this model in a preliminary report (Mosier et al, 1992, AIDS Res. Hu.

Retroviruses 8:1387). Anti HIV neutralizing antibody has been shown by passive immunization in this SCID hu model to afford some protection (Parren et al 1995, AIDS 9(6): F1–6).

An interesting finding for p17, one of the two major gag proteins, involves the 30 amino acid peptide HGP-30, whose sequence contains T and B cell epitopes immunoreactive with p17 of HIV (Sarin et al 1986, Science 232:1135; Naylor et al 1987, Proc Nat. Acad Sci 84:2951–5). See also U.S. Pat. No. 4,983,387 to Goldstein, et al, the entire disclosure of which is incorporated herein by reference thereto. This peptide of p17 known as HGP-30 has the following sequence:

```
Y S V   H Q R   I D V   K D T   K E A    (SEQ ID NO:1)

L E K   I E E   E Q N   K S K   K K A
```

HGP-30 has been conjugated to a large protein, Keyhole Limpet Haemocyanin (KLH), and found to be immunogenic in various animals and man, and the conjugate is well tolerated in both animals and humans (Gazzard et al, 1992, Vaccine Res. 1:129; Sarin et al, 1994, Vaccine Res. 3:495; Kahn 1992, AIDS Res Hu Retroviruses 8:1321; Naylor et al 1991, Int J. Immunopharm 13(Suppl):117). A pilot study of HGP-30 vaccine has shown protection from HIV infection in such SCID hu mice given PBL from HGP-30 immunized donors (Sarin et al 1995, Cell Molec Biol 41:401). More recently it has been shown that the presence of a predominance of IgG3 antibodies in serum of HGP-30 vaccine immunized human donors correlates with protection by PBL in the SCID Hu mouse HIV virus challenge model (Kahn et al 1996, Abstract 13 International AIDS Conference, Vancouver, Canada, July 1996; Talmadge et al 1996, Clin Immunol, Meeting New Orleans La. June 1996). This is thought to be quite different than what would be found if SCID hu mice with PBL from hyperimmunized env gp120 donors who had high titers of antibodies to the envelope protein where similarly infected with HIV; in this case it is expected that there would be afforded little or no protection.

With the recent recognition of the need to specifically direct the immune response various methods are under investigation. Use of protein carriers to direct nature of the immune response such as antibody, TH1, TH2, TS subclass of antibodies and CTL is now being characterized. Conjugation of HIV to Brucella abortus has been used to stimulate IgG2a in mice with the goal of stimulating IgG3 in humans, as shown by the following quote from the authors:

". . . From a functional point of view, IgG3 is the human counterpart of murine IgG2a . . . "

Golding et al, 1991, AIDS Res HU Retroviruses 7:435. This is based upon the evidence part of which was previously cited, namely, Pound et al, ibid, Weiner et al, ibid, Jeffries et al, ibid.

Considering the correlation of human IgG3 to murine IgG2a suggested by Golding et al, 1991, ibid the following considerations are also relevant. Protein antigens induce IgG1, IgG3 and IgG4 in man and IgG1 and IgG2 in mice (Hammarstrom et al, 1990, Chapt 15, p.301, in Shakib ed., ibid). Allergens induce IgG4 and IgE in man (and IgG1 and IgE in mice (Snapper, 1990, in Shakib ed., ibid). Carbohydrates induce IgG3 in mice and IgG2 in man (Hammarstrom et al, ibid). ADCC are associated with IgG1 and IgG3 in man and IgG2 in mice (Pound et al, 1990, in Shakib ed., ibid). Complement binding activities are associated with IgG1 and IgG3 for man and IgG2a and IgG2b in mice (Hammarstom et al ibid; Pound et al, ibid). TH1 cytokines such as interferon γ inhibit IgG1 in man (Kawano et al, 1994, J. Immunol. 153:4948) and IgG1, IgG2a, and IgE in mice, and IgG2a in mice (Snapper, ibid). IL-4 and IL-5 which stimulate TH2 responses stimulate IgG1 and IgE in mice, and IgG1 and IgE in man (Lundgren et al 1989, Eur J Immunol 19:1311; Snapper et al, ibid).

The use of adjuvants to direct immune response to a cellular or humoral pathway has shown that in the mouse alum directs the system towards IgG1 production and a poor DTH response whereas Freund's complete adjuvant induces a slightly stronger DTH and IgG2a response (Hadjipetrou-Kourounakis et al, 1984, Scan J. Immunol 19:219; Kenney et al, 1989, J. Immunol. Meth 121:157–66; van de Wihgert et al, 1991, Infect Immun 59:2750; Golding et al, 1994, Am J. Trop. Med Hyg. 50(4) (suppl):33)). The route of administration for TH1 or TH2 directed by adjuvants from Syntex SAF-1 and RIBI has also been reported (Golding et al, 1994, ibid). Likewise, the use of cytokines in vaccine formulations has also been evaluated and although showing promising results such use of cytokines in vaccines are likely to be limited (Lachman et al, 1995, AIDS Res Hu Retroviruses 11(8):921; Bui et al, 1994, J. AIDS 7:799).

Traditionally, small peptides must be attached to carrier proteins in order to elicit immune responses. Often a large protein such as KLH is used. However, it has been observed that heterogenous (impure) KLH yielded a better immune response than did a more homogenous preparation (Herscowitz et al, 1972, Immunol. 22:51). Consider also that in man KLH induces IgG1 and IgG2 in early stages and also IgG4 after prolonged immunization (Bird et al, 1990, Immunology 69:355–360). Similiar observations with KLH conjugates were reported by Zimmerman et al, 1996b ibid. This is in spite of the fact that there is a need for a directed response with IgG3 as a marker (McDougal et al 1989 ibid; Kahn et al, 1996, ibid). It is desirable to find other methods to direct the response primarily or substantially to murine IgG2a or human IgG3, a TH1 associated pathway. The present inventors recognized that the carrier should not be directing the response in an undesired direction and since the KLH molecule seems to be predominantly directing the response in the TH2 direction it was concluded that another carrier should be considered. Likewise, other factors such as costs, ease of manufacture, and stability, helped lead to the discovery of this invention.

There is no evidence that changing the nature of a peptide, such as by addition(s) or deletion(s) of one or several amino acids and/or method of attachment to a carrier could or would influence the subclass of antibody generated that recognize the epitope even though it is known that such manipulations can induce different responses such as the stimulation of B and T cells, cytotoxic and lymphoproliferative responses. However, the effect of T cell epitopes on antibody responses that has been reported has been for the presence or absence of antibody production by helper or suppressor immune responses (Sercarz et al, 1991, Immunol Today 12:111; Yowell et al, 1979, Nature 279:70; Wicker et al, 1984, Eur J. Immunol. 14:442).

Zimmerman et al (1996a,b, Vaccine Res 5:91–102, 103–118; WO 89/12458, the disclosures of which are incorporated herein in their entireties, by reference thereto) have taught that addition of a TCBL to a peptide epitope could alter the nature of the immune response (i.e., TH1 or TH2). They further showed that the antibodies derived from use of heteroconjugates were better able to recognize the native molecule than were the antibodies prepared by using a peptide-KLH conjugate. It was shown that the antibodies induced by the heteroconjugate had a broader specificity, so that they recognized the peptide epitope not only in the linear form, but also in the native molecule which should offer a number of advantages. Indeed, it was shown that the antibodies in some cases generated as a result of the use of the peptide conjugated to KLH were not able to recognize the epitope in the native molecule. Where comparisons exist this contrasts with the results of Vordermeier et al (1995, Vacc 13:1576). They showed that antibodies raised to the peptide epitope or to the recombinant protein 38 KD expressed in a bacterial system. This 38 KD protein (with the primary mycobacterium amino acid sequence, also had a leader sequence and was not processed as was the native protein in the Mycobacterium infected cell, such as, addition of carbohydrates, lipids and phosphorylated or sulfonated, were not able to recognize the native protein and were not protective upon challenge.

Prior work has established that p17 can be subdivided into several peptides for induction of immune responses (Goldstein et al, U.S. Pat. No. 4,983,387; Sarin et al, EP 0 246 829; Jiang et al, 1992, J. AIDS 5:382). That and other work has shown that in the p17 molecule numerous immunological epitopes are predicted to be present or experimentally determined (Naylor et al, 1990, Mono. Viro 18:74; Coates et al, 1987, Nature 326:549; Wahren et al, 1989, J AIDS 4:448; Broliden et al, ibid; Papsidero et al, 1989, J. Virol 63:267; Boucher et al, 1990, Clin Lab Anal 4:43). However, these reports studied total antibody response, cytotoxic T cell or lymphoproliferative responses. Other work has shown that certain conjugates which include a T cell binding ligand (TCBL) and an epitope of interest from a disease associated antigen can also have biological activity even when the epitope alone is inactive (Zimmerman et al 1996a,b, ibid). Since in man KLH induces IgG1 and IgG2 in early stages and also IgG4 after prolonged immunization (Bird et al, ibid) it is desirable to use other methods to direct the response to IgG3, a TH1 associated pathway, since the need for a directed response with IgG3 as a marker is well documented (McDougal et al, 1988, ibid; Kahn et al 1996, ibid).

SUMMARY OF THE INVENTION

The present invention relates to certain heterofunctional, immunological conjugates comprising at least two T cell specific binding ligands covalently linked together, wherein one of the TCBLs binds to a specific class or subclass of T cells and another of the T cell specific binding ligands is an antigenic peptide of from about 25 to about 37 amino acids (which may be referred to hereinafter as "modified HGP-30") and which is capable of eliciting TH1 associated antibodies when administered to a human in need thereof, wherein the antigenic peptide has sequence homology with the amino acid sequence beginning at from position 75 to position 82 of p17 gag protein of HIV and extending to from position 106 to position 110 of p17 gag protein of HIV.

The antigenic peptides used as the other of the T cell specific binding ligands in the heterofunctional conjugates of this invention are the subject matter of the present applicants commonly assigned copending application titled "Modified HGP-30 Peptides, Conjugates, Compositions and Methods of Use" and filed on even date herewith under attorney's docket no. CELL-100 (hereinafter may be referred to as "companion application"). The disclosure of this companion application is incorporated herein by reference thereto.

More particularly, the antigenic peptides of p17 include at least the first through at least the 22nd amino acids of HGP-30 and, preferably, the first to 26th or 27th amino acids of HGP-30 and extending from the first amino acid (i.e., N-terminal) for at least three and up to about 10 amino acids at the C-terminal end of the specific adjacent peptide of p17, referred to as HGP-34;

In particular, the antigenic peptides useful in this invention will generally be between about 25 and 37 amino acids as represented in the following extreme and representative cases:

```
A T L  Y S V  H Q R  I D V  K D T   (SEQ ID NO:2)
K E A  L E K  I E E  E
S L Y  N T V  A T L  Y S V  H Q R   (SEQ ID NO:3)
I D V  K D T  K E A  L E K  I E E
E Q N  K S K
R S L  Y N T  V A T  L Y S  V H Q   (SEQ ID NO:4)
R I D  V K D  T K E  A L E  K I E
E E Q  N K S  K
```

A particularly preferred antigenic peptide for use in this invention has the following amino acid sequence

```
A T L  Y S V  H Q R  I D V  K D T   (SEQ ID NO: 5)
K E A  L E K  I E E  E Q N  K S
``` hereinafter sometimes may be referred to, for convenience, as m-HGP-30, representing a modified version of HGP-30. More generally, as noted above, however, all of the antigenic peptides for use in the present invention may, for convenience, be referred to generically as "modified HGP-30."

These heteroconjugates offer the advantages previously seen with other heteroconjugates (Zimmerman et al, 1996a, b, ibid; WO 89/12458, and in the commonly assigned copending application Ser. No. 08/354,751, filed Dec. 8, 1994, as a continuation of Appln Ser. No. 08/354,751, filed Dec. 8, 1994, which in turn is a continuation of prior applications Ser. Nos. 07/985,750, 07/731,394, and 07/206, 831, filed Dec. 4, 1992, Jul. 17, 1991, and Jun. 14, 1988, respectively, the disclosures of which are incorporated herein in their entireties by reference thereto) of inducing broad spectrum antibodies and of a desired TH1 specificity and incorporate a CTL epitope of the modified HGP-30 which, as shown in the companion application, may modify the response to the desired isotype but with the disadvantage of possessing restricted antibody specificity.

The present invention also relates to pharmaceutically effective compositions containing such heterofunctional antigenic peptide-T-cell binding ligand conjugates (for convenience, may sometimes be referred to as "heteroconjugate") for eliciting immunization to infection against Human Immunodeficiency Virus, HIV, in a human subject. Such compositions, in addition to the heteroconjugate of this invention will, preferably, include suitable immunological adjuvant.

Similarly, the invention relates to a method for treating or preventing HIV infection and Acquired Immunodeficiency Complex (AIDS) by administering to a human patient in need thereof, a therapeutically or prophylactively effective amount of the heterofunctional conjugate as defined above.

DETAILED DESCRIPTION OF THE INVENTION AND PREFERRED EMBODIMENTS

For the peptides disclosed above and below and as employed in the experimentation described herein, the amino acid sequences thereof, are set forth by the single identification letter symbol as follows:

| Amino Acid | Three-letter abbreviation | One-letter symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In addition to recent discoveries leading to the conclusion that HIV p17 is located near the surface of the HIV virion rather than in the internal core as in the case of p24 gag protein, it has been shown that the p17 gag protein is myristylated at its N-terminal; see, e.g., the aforementioned EP 0 245 829, incorporated herein by reference thereto. Furthermore, analysis of the peptide (designated HGP-30), which is located nearer to the C-terminal of p17, suggests that this peptide contains an immunodominant B-cell epitope which could induce antibodies that mediate cytotoxicity through ADCC type mechanisms. On the other hand, the peptide designated HGP-34 at amino acid positions 51–84, has an amino acid sequence consistent with a T-cell epitope, therefore capable of eliciting a T-cell immunological response. Analysis of the intermediate region peptide of p17 at positions 33–50 (also designated HGP-18), near the N-terminal end suggests that this peptide has the appropriate balance of hydrophilicity and hydrophobicity to constitute a transmembrane region peptide if the appropriate charge neutralizing membrane proteins are present.

It is well known that HGP-30 contains regions with well defined B cell epitopes and other regions with defined T cell epitopes (defined as epitopes stimulating lymphoproliferation and others that stimulate cytotoxic T cells) (e.g., Jiang et al, ibid). The B cell epitopes are based upon stimulating the production of antibodies, presumably IgG1 in mice, or of being recognized by antibodies in seropositive individuals. No discrimination as to subclasses in man is made. It was reasoned that if IgG3 in man or IgG2a in mice were the desired type of antibodies and an indicator of the arm being stimulated (TH1 or TH2), then to include several residues from the T cell epitope region at the amino terminus may be of benefit along with deletion of several residues at the carboxyl terminus including all or part of the B cell epitope region. Therefore, the inventors prepared and studied a peptide by modifying HGP-30, and specifically, m-HGP-30 was studied. It was reasoned that T cell epitopes such as Cytotoxic T Cell epitopes might not be suppressive but could be directing the response toward a TH1 response. That being the case the inventors postulated that since TH1 correlates with cellular mechanisms of immune responses, the TH1 effect includes not cytotoxic cells, but antibody dependent cellular cytotoxicity (ADCC) and complement binding, both of which are properties of IgG2a in the mouse and IgG3 in man. Therefore, the antibody response induced is towards IgG2a. For more details on HGP-30 and the immune response to the various epitopes see e.g., Gazzard et al, 1992, Vaccine Res. 1:129; Sarin et al, 1994, Vaccine Res. 3:49; Willer et al, 1992, Biomed. & Pharmacol. 46:359; Naylor et al, 1991, Int. J. Immunopharm. 13(Suppl 1):117; Jiang et al 1992, AIDS Res. 5:382; Kahn et al, 1992, AIDS Res & Human Retroviruses 8:1321. See also U.S. Pat. No. 4,983,387. The disclosures of these documents are incorporated herein in their entireties by reference thereto. In particular, the modified HGP-30 with these goals that was used to prepare the heterofunctional conjugates was m-HGP-30, i.e., SEQ ID NO:5 as follows.

A T L  Y S V  H Q R  I D V  K D T    (SEQ ID NO: 5)
K E A  L E K  I E E  E Q N  K S

More particularly, the modified HGP-30 antigenic peptides of p17 include at least the first through at least the 22nd amino acids of HGP-30 and, preferably, the first to 26th or 27th amino acids of HGP-30 and extending from the first amino acid (i.e., N-terminal) for at least three and up to about 10 amino acids at the C-terminal end of the specific adjacent peptide of p17, referred to as HGP-34;

In particular, the antigenic peptides useful in this invention will generally be between about 25 and 37 amino acids as represented in the following extreme and representative cases:

A T L  Y S V  H Q R  I D V  K D T    (SEQ ID NO:2)
K E A  L E K  I E E  E

S L Y  N T V  A T L  Y S V  H Q R    (SEQ ID NO:3)
I D V  K D T  K E A  L E K  I E E
E Q N  K S K

```
                              -continued
R S L  Y N T  V A T  L Y S  V H Q    (SEQ ID NO:4)

R I D  V K D  T K E  A L E  K I E

E E Q  N K S  K
```

It should be understood that in any of the above amino acid sequences of the antigenic peptides variations of specific amino acids which do not adversely effect the desired biological activity are contemplated and fall within the scope of the invention. In particular, it is recognized that the foregoing sequences are based upon a specific variant of HIV, namely, HIV-1SF2 (actually, the Ser[86] analog) and, although this region of interest of HIV is generally fairly highly conserved, other naturally occurring and spontaneously occurring variants, include from one or several (e.g., up to about 10) variations of the amino acids within the sequence of interest. Such natural and spontaneously occurring amino acid variations are specifically contemplated and, in certain cases, it may be advantageous to use mixtures of peptides, the sequences of which, within the guidelines given above, and discussed in more detail below, correspond to two or more natural and spontaneously occurring variants of HIV.

Still further, as well recognized in the art it is often advantageous to make specific amino acid substitutions in order, for example, to provide specific binding sites or for purpose of introducing radioactive or fluorescent tagging of the peptide. Such "designed" amino acid sequences are also within the scope of the antigenic peptides (i.e., modified HGP-30) of this invention.

Examples of different consensus sequences of HIV which are also specifically included within the scope of the modified HGP-30 antigenic peptides for use in the heterofunctional conjugates of this invention include, for instance, the following, wherein the lower case letters represent potential or known cites of amino acid variability resulting from the allelic variations, genetic drift and mutations of the particular consensus sequence; the presence of a "?" symbol reflects that there is no agreed upon consensus for the amino acid at that position of the consensus sequence:

```
CONSENSUS A:
kSL fNt vat LyC vHq rId           SEQ ID NO:6 vkD tKe Ald kiE eiq nks k

CONSENSUS B:
rSL yNt vat Lyc VHq rIe           SEQ ID NO:7

VkD tKe Ald kiE eEq nks k

CONSENSUS C:
rSL ?Nt vat LyC vH? ?Ie           SEQ ID NO:8 vrD tKe Ald kie eEq nk? Q

CONSENSUS D:
kSL ?Nt vat LYc VHe rIe           SEQ ID NO:9 vkd tKe Ale kmE eEq nks k

CONSENSUS F:
rSL ?Nt v?v Lyf vHq rvE           SEQ ID NO:10 vkD TKE ALd KLE EEQ NKS q

CONSENSUS G:
kSL ?N? ?a? L?C ?Hq rI?           SEQ ID NO:11 vkD tke Ale EVE Kaq kns k

CONSENSUS H:
QSL fNl la? LyC vHq rId           SEQ ID NO:12

?kD tKe Al? k?? E?Q N?? Q

CONSENSUS O:
?SL WNA I?V LWC vHN r??           SEQ ID NO:13

I?D tQQ AIQ kLK eVM ?SR K
```

For example, for Consensus sequence A, above, the following species have been identified; the dashes represent identity of amino acid with the consensus sequence [it is noted, however, that only amino acids at positions 74 to 93 are identified; the amino acids at positions 94 to 111 or higher at the C-terminal end or at positions 73 and below at the N-terminal end may be readily determined from the published sequences; the same applies to the exemplary species for Consensus sequences B, C, D]:

```
CONSENSUS.A kSL fNt vat LyC VHq rId vk  SEQ ID NO:6

HIV-1U455   R-- Y-T VAV -Y- --Q R-D VK  SEQ ID NO:14

HIV-1MAL    K-- Y-T VAT -Y- --Q R-D VK  SEQ ID NO:15

HIV-1TN243  K-- F-T VAT -W- --Q R-E VK  SEQ ID NO:16
```

The following are examples of Consensus Sequence B above:

```
CONSENSUS.B rSL yNt vAt LYC vHQ rIe vk  SEQ ID NO:7

HIV-1SF2    R-- Y-T V-T --- V-- R-D VK  SEQ ID NO:17

HIV-1TB132  R-- Y-T I-V --- V-- K-E VK  SEQ ID NO:18

HIV-1LAI    R-- Y-T V-T --- V-- R-E IK  SEQ ID NO:19

HIV-1HXB2R  R-- Y-T V-T --- V-- R-E IK  SEQ ID NO:20

HIV-1MN     K-- Y-T V-T --- V-- K-E IK  SEQ ID NO:21

HIV-1JH3    K-- F-T V-T --- V-- R-E VK  SEQ ID NO:22

HIV-1JRCSF  T-- Y-T V-T --- V-- R-E IK  SEQ ID NO:23

HIV-1OYI    R-- Y-T V-T --- V-- K-E VK  SEQ ID NO:24

HIV-1NY5CG  R-- F-T V-V --- V-- R-D VK  SEQ ID NO:25

HIV-1NL43   R-- Y-T I-V --- V-- R-D VK  SEQ ID NO:26

HIV-1CDC4   R-- Y-T V-T --- V-- R-E VR  SEQ ID NO:27

HIV-1HAN    R-- Y-T V-T --- V-- K-E VK  SEQ ID NO:28

HIV-1CAM1   R-- Y-T V-T --- V-- K-D KV  SEQ ID NO:29

HIV-1RF     K-- Y-A V-T --- V-- N-E VR  SEQ ID NO:30

HIV-1D31    R-- F-T V-T --- V-- R-E VK  SEQ ID NO:31

HIV-1BH102  R-- Y-T V-T --- V-- R-E IK  SEQ ID NO:32

HIV-1PV22   R-- Y-T V-T --- V-- R-E IK  SEQ ID NO:33

HIV-1JRFL   R-- Y-T V-T --- V-- R-E VK  SEQ ID NO:34
```

The following are exemplary of the sequences for species of Consensus Sequence C:

```
CONSENSUS.C rSL ?Nt vat Lyc VH? ?ie vr SEQ ID NO:8

HIV-1ZAM18  K-- F-T VVT -WC --E DIT VR SEQ ID NO:35

HIV-1ZAM19  K-- H-A VAV -YC --K XIT VR SEQ ID NO:36

HIV-1ZAM20  R-- Y-T VAT -YC --A GIE VR SEQ ID NO:37
```

Consensus Sequence D includes the following exemplary species:

```
CONSENSUS.D kSL ?NT VAT LYC VHe RiE VK SEQ ID NO:9

HIV-1ELI    R-- Y-- --- --- --K G-D -K SEQ ID NO:38

HIV-1Z2Z6   R-- F-- --- --- --E R-E -K SEQ ID NO:39

HIV-1NDK    R-- Y-- --- --- --E R-E -K SEQ ID NO:40
```

Similarly, other naturally occuring species within Consensus A, Consensus B, Consensus C, Consensus D, as well as Consensus F, Consensus G, Consensus H, Consensus O, whether presently known or existing, or subsequently discovered or subsequently arising, can be used as the modified HGP-30 antigenic peptide of this invention. It is well known in the art that these various consensus sequences are generally derived from, and are prevalent in different geographical regions of the world and are often referred to as "clades" (also known as "subtypes") of the HIV virus. Representative of these clades of modified HGP-30 include the following partial consensus sequences, i.e., positions 85–114, (wherein the letter designations next to the country names generally correspond to the consensus sequences as given above) and any allelic variations thereof:

```
Thailand-B:
YCV HQK IEV KDT KEA LEK IEE EQN KSK KKA      SEQ ID
                                             NO:41
Thailand-A/E:
WCV HQR IEV KDT KEA LDK IEE VQN KSQ QKT      SEQ ID
                                             NO:42
Uganda-A:
YCV HQR IDV KDT KEA LNK IEE MQN KNK QRT      SEQ ID
                                             NO:43
Kenya-A:
YCV HQR IDV KDT KEA LDK IEE IQN KSK QKT      SEQ ID
                                             NO:44
Brazil-A/E:
YFV HQR VEV KDT KEA LDK LEE EQN KSQ QKT      SEQ ID
                                             NO:45
Brazil-B:
YCV HQK IDV RDT KEA LEK VEE EQN KSK EKA      SEQ ID
                                             NO:46
Uganda-B:
YCV HQR IDV KDT KEA LDK IEE EQN KSK KKE      SEQ ID
                                             NO:47
Uganda-C:
YCV HKG IEV RDT KEA LDK IEE EQN KIQ QKT      SEQ ID
                                             NO:48
India-C:
YCV H?? IEV RDT KEA LDK IEE EQN K?Q QKT      SEQ ID
                                             NO:49
Uganda-D:
YCV HER IKV ADT KEA LDK IEE EQT KSK KKA      SEQ ID
                                             NO:50
```

As can be seen from the above aligned consensus sequences and species for the various consensus sequences, there is some variation amongst HIV subtypes in the gag protein sequence. Moreover, there is considerable variation in the specific numbering of amino acids among different HIV strains. In the present invention, the numbering of sequences is based on the sequence of HIV strain 1SF2 or MN; however, it is the amino acid sequence itself, allowing for variations observed amongst HIV subtypes, that is important. The sequences listed above are illustrative of the types of amino acid changes that can be made in the antigenic modified HGP-30 peptides of the invention and the conjugates based thereon. In addition to the variations in the amino acids among the various HIV strains, it is also recognized that the amino acids at the N-terminal and C-terminal may be present as the free acid (amino or carboxyl groups) or as the salts, esters, ethers, or amides thereof. In particular amide end groups at the C-terminal and acetylation, e.g., myristyl, etc. at the N- or C-terminal, are often useful without effecting the immunological properties of the peptide.

The peptides of the present invention can be prepared by conventional processes for synthesizing proteins, such as, for example, solid phase peptide synthesis, as described by Merrifield, R. B., 1963, J. of Am. Chem. Soc., 85:2149–2154, incorporated herein by reference thereto. It is also within the scope of the invention and within the skill in the art to produce the novel peptides of this invention by genetic engineering technology.

In the present invention, the above modified HGP-30 antigenic peptides are conjugated to a T cell binding ligand (TCBL). Various T Cell Binding ligands (TCBL) that can be used include those shown in Table 1, below. These include, for example, peptide J from β-2-microglobulin 35–50 (Parham et al, 1983, J Biol Chem. 258:6179; Zimmerman et al, WO 89/12458); TCBLs from MHC class 1 α3 domain positions 223–229 (Salter et al, 1990, Nat 345:41), the MHC class II β2 domain 135–149 (Konig et al, 1992, Nat 356: 796; Cammarota et al, 1992, Nat 356:799) or Interleukin Iβ 163–171 (Nencioni et al, 1987 J. Immunol. 139:800; Zimmerman et al, 1996a,b, ibid). Other TCBLs include, for example, those mentioned in the aforementioned WO 89/12458. Guidelines for selection of these or other TCBLs are discussed therein as well as in the Zimmerman et al 1996a,b, ibid articles, incorporated herein by reference. Mention may be made of, for example, the molecules known as B7 (Freeman et al, Science 262:909); B70 (Azuma et al, 1993, Nature 366:76); GL1 (Hathcock et al, 1993, Science 262:905); CD58 (Arulanandam et al, 1993, Proc. Nat. Acad. Sci. 90:11613), CD40 (van Essen et al, 1995, Nature 378:620); and ICAM-1 (Becker et al, 1993, J. Immunol. 151:7224). The reader is referred to these literature articles for further details of these TCBLs.

TABLE 1

TCBL Peptides used in Heteroconjugate Construction
Name/Amino Acid Sequence Molecule/a.a. positions

| MHC Class I | MHC $I_{\alpha 3}$ | |
|---|---|---|
| DQT QDT E | 223–229 | (SEQ ID NO: 51) |

TABLE 1-continued

TCBL Peptides used in Heteroconjugate Construction
Name/Amino Acid Sequence Molecule/a.a. positions

| | | |
|---|---|---|
| Lymphokine | IL-1$_\beta$ | |
| VQG EES NDK | 163–171 | (SEQ ID NO: 52) |
| MHC Class II | MHC-II$_{\beta 2}$ | |
| NGQ EEK AGV VST GLI | 135–149 | (SEQ ID NO: 53) |
| β-2-Microglobulin | β-2-M | |
| DLL KNG ERI EKV E | 35–47 | (SEQ ID NO: 54) |

Heteroconjugates prepared by use of these antigenic peptides based on the modified HGP-30 epitopes and TCBL ligands have been shown by the inventors to elicit an immune response to HIV that can be directed toward the desired TH1 as evidenced by the numerous examples of the TH1 characteristic antibody IgG2a (mouse) or thereby IgG3 (man). The order of the TCBL and modified HGP-30 peptide is not usually critical and may be reversed. For example, if TCBL=A and modified HGP-30=B then the heteroconjugate may have the sequence A-B or B-A. Also, while the TCBL and modified HGP-30 may be directly coupled to each other, in some cases a small linker sequence or a larger heterolinker molecule may be used to couple the two peptides. For example, as the spacer, one or a few, up to about 5, preferably, up to about 3, neutral amino acids, such as glycine, may be used to link the peptides in the heteroconjugate. A preferred spacer peptide is GGG, however, the spacer may be made larger or smaller and altered to include other molecules besides the amino acid glycine. As examples of heterolinkers mention may be made of, for example, N-succinimidyl-3-(2-pyridylthio)propinate (SPDP), m-maleimidobenzoyl-N-hydroxy-succimide (MBS) as well as any of the other reagents employed to link peptides, including without limitation those disclosed in the aforemention WO 89/12458, incorporated herein by reference.

The following are exemplary of applications for various embodiments of the heterofunctional conjugates of the invention but, it is understood that the invention is not restricted to the following described examples.

Embodiment 1. Use of the heteroconjugate of e.g., Peptide J and the modified HGP-30 sequence to direct the immune response as a prophylactic vaccine for a TH1 directed immune response to prevent the infection by HIV.

Embodiment 2. Use of the heteroconjugate to direct the immune response as a therapeutic vaccine for a TH1 directed immune response in HIV infected persons perhaps in conjunction with other therapies to reduce viral load and to control or cure the infection by HIV.

Embodiment 3. Use of a TCBL as a carrier for the modified HGP-30 sequence to direct the immune response as a prophylactic vaccine to induce a TH1, TH2 or mixed TH1/TH2 directed immune response to prevent the infection by HIV.

Embodiment 4. Use of a TCBL as a carrier for the modified HGP-30 sequence in the heteroconjugate to direct the immune response as a therapeutic vaccine to induce a TH1, TH2 or mixed TH1/TH2 directed immune response against the HIV virus and virus infected cells in HIV infected persons perhaps in conjunction with other therapies to reduce the viral load and to control or cure the infection by HIV.

Examples of other therapies which may be used in conjunction with the heteroconjugates of this invention include, for example, proteas inhibitors, reverse transcriptase inhibitors and the like.

Examples
I. Peptides

The T cell binding ligand (TCBL) of the heteroconjugate used in these studies includes a region of β-2 microglobulin, Peptide J (Parham et al, 1983, ibid) shown underlined for a MHC Class I-like action PEPTIDE J DLL KNG ERI EKV EGG C-amide SEQ ID NO:55

The heteroconjugate with the modified HGP-30 sequence and the above TCBL contained a spacer of one additional glycine substituted for the C-terminal cysteine for a total of three glycine residues. Accordingly, the heterofunctional conjugate had the following formula Peptide JH: DLL KNG ERI EKV EGG   SEQ ID NO:56

<u>GAT LYS VHQ RID VKD TKE</u>

<u>ALE KIE EEQ NKS</u> wherein the underlined portion represents m-HGP-30.

The peptides were all synthesized by Quality Controlled Biochemicals, Inc. (QCB) (Hopkinton, Mass.) using the FMOC procedure and a double coupling protocol for the first 8 residues. Usually the peptide is prepared with the carboxyl terminus as an amide form. All of the peptides were purified at QCB using preparative HPLC, and analyzed by an analytical HPLC, amino acid analysis and mass spectrophotometer. The peptides were greater than 95%, usually greater than 98%, pure by HPLC criteria. The dry peptides obtained from QCB were stored in glass vials with desiccant at −20° C.

II. Preparation of Conjugates

KLH Conjugations

Keyhole Limpet Haemocyanin (KLH) (Pierce) may be conjugated to the HGP-30 or modified HGP-30 peptide by a glutaraldehyde conjugation method (Naylor et al 1987, Proc. Nat. Acad. Sci. 84:2951. KLH may also be conjugated to HGP-30 via the EDC method as described above. The alternative conjugation techniques are useful to evaluate if the method of conjugation was important as far as the nature of the immune response evoked. In both cases a 1:1 mg weight ratio of peptide to KLH is used. Conjugation of the antigenic peptide to KLH may also be carried out by formation of a thioether using a halogenated N-terminal acetyl derivative (Linder et al, 1987, Int. J. Peptide Chemistry, 30:794; Robey et al, 1989, Anal. Biochem. 177:373; Kolodny et al, 1990, Anal. Biochem. 187:136; and Robey et al, U.S. Pat. No. 5,066,716). To reduce any oxidized sulfhydryls or disulfides that may form during storage, the resulting dissolved T cell binding ligands (TCBL) are added to an equal molar quantity of tris-(2-carboxylethyl)phosphine (TCEP) (Pierce, Rockford, Ill.), which is dissolved to a concentration of 3.5 mg/ml in 0.2 M sodium phosphate buffer (pH 6.8). Next, 50 μl of 0.1 M ethylenediaminetetraacetic acid disodium (EDTA) is added to give a final concentration of 0.005 M. The mixture is then gassed with nitrogen, and allowed to incubate with stirring using a "V" shaped stir bar in a sealed screw cap plastic conical reaction vessel (total container volume 1.5 ml) for at least 45 minutes, but usually less than 120 minutes, at room temperature. In the Thioether protocol, the KLH is treated with TCEP, and separated using a P6DG column (Bio-Rad). The HGP-30 peptide and KLH are allowed to incubate for 18 hours to allow conjugation to occur. Then the reaction mixture is exhaustively dialyzed against 3–4 changes of 1 L each change of PBS over 3–5 days and the product is sterile filtered (0.2μ low protein binding filter).

The heteroconjugate may be synthesized as a single peptide without any conjugation step or by conjugation of the TCBL and the modified HGP-30 by using the thioether method or by any other conjugation method known to the skilled practitioner.

The final products, the peptide, heteroconjugate, peptide-KLH control, are analyzed for protein or peptide using the BCA protein assay, and adjusted to contain between 200–400 μg/ml of total protein or peptide, and stored frozen (−20° C.) in 1.5 ml aliquots ready for thawing and administered in combination with an adjuvant (e.g., alum, ICFA, SAF-1) or carrier (e.g., liposomes or Novasomes).

III. Immunization, Anti-sera Collection and Processing

In a series of experiments, groups (5–10 per group) of 10–16 week old BALB/c female mice (Taconic Farms, Germantown, N.Y.) are immunized and test bled according to the following schedule. Schedule A immunizations on day 0, day 7, test bleeding on days 14, 28 and 42.

The antigens are prepared with adjuvants and carriers as follows. The antigens are emulsified as previously described (Zimmerman et al, 1996a,b, ibid) for Incomplete Freund's adjuvant (Life Technology, Gaithersburg Md.) supplemented with Muramyl Dipeptide (Pierce). Other adjuvants, which may be used include, for example, alum (Pierce, Gensia, Inc. San Diego, Calif.), Ribi (Immunochem Research Inc. Hamilton, Mont.) and a proprietary adjuvant "Novasomes" (Novavax, Rockville Md.). These adjuvants and carrier systems are used according to the manufactures' direction. The Novasome system is evaluated with or without a Lipid A supplement.

Unanesthetized mice are placed in the palm of one hand with the nape held between the thumb and forefinger, and the little finger wrapped around the lower abdomen. The mice are inoculated with 0.2–0.4 ml of the emulsion equally divided between a subcutaneous site in the nape of the neck and intraperitonealy in the lower abdomen. Other routes which could be used include subcutaneously, intramuscularly, etc. The inoculum contains 250 μg/ml of KLH conjugate, heterofunctional conjugate or peptide alone, unless otherwise stated.

The mice are anesthetized by Metofane™ (Pitman-Moore Mundelein, Ill.) for retrorbital bleeding and ear tagging. Blood from individual mice on the specified days is collected from the retrorbital vein using a 5¾" glass pasteur pipette, transferred to 1.5 ml centrifuge tube and allowed to clot. The clots are separated from the walls of the tube by use of a flexible thin wire extending to the bottom of the tube and encircling the inner circumference of the tube, and the cells/and clot are separated by centrifugation from the sera. The sera from individual animals are collected and placed in labeled storage vials and stored frozen until ready for testing. At the first time of blood collection, each mouse is also ear tagged for identification purposes with an aluminum band imprinted with a unique sequential number (National Band and Tag, Lexington, Ky.).

IV. ELISA Assays

The sera is tested for the presence of antibody by an indirect ELISA. In this procedure, high binding plates (Maxi Sorb; Nunc, Naperville, Ill.) are used. The plates are coated at 4° C. with the HGP-30 (SEQ ID NO:1) or modified HGP-30 (SEQ ID NO:5) from a different preparation or a control peptide at a concentration of 1.0 μg/ml in 0.15 M bicarbonate coating buffer (pH 9.6) using 118 μl/well, and stored at 4° C. for 1–7 days. Prior to use, the wells are washed at least 2 times with PBS containing 0.05% Tween™ 20 (PBSTw), blocked with 150 μl of 0.2% bovine serum albumin (BSA) (Sigma Chemicals St Louis, Mo.) in PBSTw for 15–30 minutes, and washed at least two more times with PBSTw. Antibodies to the coating HGP-30, modified HGP-30 or a control peptide in the sample are assayed as follows. The control peptide used in this case is derived from an env V-3 peptide about 20 amino acids in length, however, as is well known in the art, other controls can be used to measure non-specific antibody response as measure of background.

First, an appropriate dilution, usually from 1:100 to 1:10,000 of the test antisera is made in 0.2% BSA in PBSTw, and 100 ml thereof is added per well. After all of the wells are loaded, the plates are sealed with an adhesive plate sealer (ICN, Costa Mesa, Calif.), and incubated for 2 hours at 37° C. The plates are then washed at least three times with PBSTw (>250 μl/well per wash) and drained. The wells are loaded with 100 μl of a dilution, usually 1:5000 in 5.0% BSA in PBSTw, of the enzyme-antibody conjugate, HRP-goat anti-murine immunoglobulins (Kirkegaard and Perry Laboratories (KPL), Gaithersburg, Md.). The plates are incubated for 1.5 hours with the enzyme-antibody conjugate before a final series of three washing steps and color development using as the substrate, 100 μl/well of o-phenylenediamine dihydrochloride (OPD (Sigma)). The substrate is prepared by dissolving a 5.0 mg tablet in 12.5 ml of urea hydrogen peroxide phosphate citrate buffer (pH 5.0). The color reaction is stopped after about 60 minutes with 100 μl of 4.0 N H2SO4, and the color is read as optical density (OD) or absorption ($A_{490}$) at 490 nanometers on an ELISA plate reader. Data is printed out and also saved on the hard drive of the computer attached to the plate reader for use in further analysis. Data points are collected in duplicates, and the values reported as the average of both readings.

As discussed below, in some cases, the second incubation (1.5 hours) is carried out with isotyping antisera of Goat anti-murine heavy chain specific class or subclass ($\mu$, $\alpha$, $\gamma 1$, 2a, 2b and 3) (Sigma or ICN), and then an enzyme conjugate, HRP-rabbit-anti-goat immunoglobulins (KPL), is used before the substrate color development step.

EXAMPLE 1

Previously it was observed that a TB related heterofunctional conjugate can stimulate a TH1 or TH2 antigen specific immune response (Zimmerman et al 1996a,b, ibid). Table 2 demonstrates that such heteroconjugate of a modified HGP-30 shows responses as an ELISA signal observable at several different dilutions starting at 1:200 to 1:6400 by testing the antisera reactivity against wells coated with either the immunizing, but unconjugated modified HGP-30 peptide or control peptide, measuring the OD, and calculating the differences between the two OD values which is indicative of specific antibody. These mice are immunized using Incomplete Freund's adjuvant at 40 μg per dose per animal. A large number of the animals produced specific antisera with a substantial titer. Whereas with the TB heterofunctional conjugate no discernable specific immune response is observed until a sensitive challenge protocol is used with the immunogenic modified HGP-30 heterofunctional conjugate, ⅔ of the animals at the dose used even as early as day 35 showed an immune response at a 1:800 dilution.

TABLE 2

Titer Anaylsis of Anti-HGP30 in heteroconjugate Immunized mice

| | Mouse Dilution - Number | | | | | | | | | | | |
|---|---|---|---|---|---|---|---|---|---|---|---|---|
| | 1/200 | | | 1/400 | | | 1/800 | | | 1/1600 | | |
| | Modified HGP-30 | Control Peptide | Net HGP-30 | Modified HGP-30 | Control Peptide | Net HGP-30 | Modified HGP-30 | Control Peptide | Net HGP-30 | Modified HGP-30 | Control Peptide | Net HGP-30 |
| Prepled | 0.090 | 0.090 | 0.000 | 0.070 | 0.070 | 0.010 | 0.050 | 0.060 | 0.000 | 0.060 | 0.060 | 0.000 |
| 512 | 0.820 | 0.110 | 0.700 | 0.490 | 0.060 | 0.430 | 0.290 | 0.060 | 0.230 | 0.150 | 0.050 | 0.100 |
| 513 | 0.610 | 0.100 | 0.510 | 0.390 | 0.080 | 0.310 | 0.230 | 0.070 | 0.160 | 0.120 | 0.070 | 0.050 |
| 514 | 0.230 | 0.110 | 0.110 | 0.140 | 0.060 | 0.080 | 0.100 | 0.060 | 0.030 | 0.090 | 0.070 | 0.020 |
| 515 | 1.330 | 0.090 | 1.230 | 1.220 | 0.070 | 1.160 | 1.080 | 0.060 | 1.020 | 0.910 | 0.060 | 0.850 |
| 516 | 1.210 | 0.110 | 1.100 | 1.030 | 0.080 | 0.960 | 0.810 | 0.070 | 0.740 | 0.590 | 0.070 | 0.520 |

| | Mouse Dilution - Number | | | | | |
|---|---|---|---|---|---|---|
| | 1/3200 | | | 1/6400 | | |
| | Modified HGP-30 | Control Peptide | Net HGP-30 | Modified HGP-30 | Control Peptide | Net HGP-30 |
| Prepled | 0.050 | 0.050 | 0.010 | 0.060 | 0.050 | 0.000 |
| 512 | 0.100 | 0.050 | 0.050 | 0.070 | 0.050 | 0.020 |
| 513 | 0.100 | 0.070 | 0.030 | 0.080 | 0.070 | 0.010 |
| 514 | 0.080 | 0.070 | 0.010 | 0.070 | 0.060 | 0.000 |
| 515 | 0.690 | 0.060 | 0.630 | 0.470 | 0.060 | 0.410 |
| 516 | 0.420 | 0.060 | 0.360 | 0.250 | 0.070 | 0.180 |

EXAMPLE 2

Three groups of mice are set up for evaluation using immunization doses of 40, 8 and 1.6 μg on day 0 and day 14 with heteroconjugates using HGP-30 preparation with the β-2-microglobulin TCBL, Peptide J. These mice are then test bled on day 35 and the sera are analyzed for the presence of an antibody immune response. Table 3 shows the results with the initial day 35 test bleed and results with antisera collected 14 days after a booster inoculation on day 42. As can be seen from Table 3, following the booster all of the animals with the higher dose responded and even several of those with the next lowest dose also responded.

TABLE 3

Dose Response with varying dose for immunization with JH heteroconjugate

| | Results of Initial Test Bleed (day 35) | | Results 14 days after Test Bleed after booster | |
|---|---|---|---|---|
| Group # | No. of animals* | No. of responders | No. of animals | No. of responders |
| 40 μg | 12 | 5 | 12 | 9 |
| 8 μg | 13 | 0 | 13 | 2 |
| 1.6 μg | 13 | 0 | 13 | 0 |

# = antigen (as specified above) in emulsion (0.2 mL) of equal parts of Incomplete Freund's adjuvant and sterile saline per animal per inoculation
* = Number of BALB/c females immunized
@ = Number of animals with specific antibody signal at 1:200 dilution of over 0.2 (>3 times the value of the control peptide)

EXAMPLE 3

In order to evaluate and identify advantageous adjuvants and carriers for use with the heteroconjugates, other than Incomplete Freund's adjuvant which is not approved by the FDA for use in man the following test is performed. A single heteroconjugate preparation JH is used at a 25 microgram dose per animal. This is used to immunize groups of mice on day 0 and 14 and then the mice are test bled on day 35. The resultant antisera are evaluated in a standard ELISA for HGP-30 specific antibody. As seen in Table 4 none of the Alum adjuvant group showed a response whereas significant numbers of animals immunized using either Incomplete Freund's Adjuvant or the Commercial formulation of TDM/MPL preparation of RIBI available from Sigma Chemicals induced an immune response. As before (Table 3) after the booster on day 42 all animals tested on day 56 for the Ribi and Freund's adjuvants demonstrated antibody response (data not shown). However, the alum heteroconjugate immunized animals were still non-responsive.

TABLE 4

Summary of day 35 response using JH heterofunctional conjugate (Peptide J as TCBL and m-HGP-30) to generate an immune resoonse with different Adjuvants

| Group # | Number of animals* | Number of responders@ |
|---|---|---|
| ALUM | 14 | 0 |
| ICFA | 12 | 9 |
| RIBI | 10 | 8 |
| No antigen or Adjuvant | 14 | 0 |

# = 25 μg of antigen in emulsion (0.2 mL) of adjuvant and sterile saline per animal per inoculation
* = Number of BALB/c females immunized
@ = Number of animals with specific antibody signal at 1:200 dilution of over 0.2 (>3 times the value of the control peptide)

EXAMPLE 4

Since the adjuvant is shown to be of some importance in eliciting an immune response another adjuvant, Novasomes, that has been described as superior (Wright et al, 1996, personal communication) is tested. In addition, since the inclusion of Lipid A is thought to be beneficial this Novasome adjuvant is evaluated with or without Lipid A addition. The Novasomes are supposed to possess many of the properties of liposomes (Fries et al, 1992, Proc. Nat Acad. Sci. 89:358) but with the added properities of ease of manufacturing and long term stability (Wright et al, ibid). As seen in Table 5 no advantage is seen using Novasomes with or without Lipid A for most antigens. Indeed, one group of animals immunized with Novasomes and the heteroconjugate had the Lipid A subset seemingly having a lower signal than does the group without Lipid A. It should be noted that often Alum is used in conjunction with the Liposomes but not enough material was available to make such a comparison.

TABLE 5

Summary for various antigens and conjugates of TCBL and KLH with HGP-30 or m-HGP-30 to generate an immune response using Novosome or Alum as adjuvant.

| Group | Number of animals | Number of responders |
|---|---|---|
| Novosomes + m-HGP-30 | 7 | 0 |
| Novosomes + m-HGP-30 with Lipid A | 7 | 0 |
| Novosomes + HGP-30 | 7 | 0 |
| Novosomes + HGP-30 with Lipid A | 7 | 0 |
| Novosomes + HGP-30-KLH | 6 | 6 |
| Novosomes + HGP-30-KLH with Lipid A | 5 | 5 |
| Novosomes + m-HGP-30 Heteroconjugate | 6 | 6 |
| Alum + m-HGP-30 Heteroconjugate with Lipid A | 6 | 0 |
| Alum + m-HGP-30 | 6 | 0 |
| Alum + HGP-30 | 6 | 0 |

In this example the animals are immunized on days 0 and 7 with the antigen and the test bleedings are taken on day 28. See legend to Table 2 for other details.

EXAMPLE 5

This example investigates the specificity of the antibodies induced by the heteroconjugate and compares the HGP-30 and modified HGP-30 KLH derived antibodies. For this purpose the heterofunctional conjugate antibodies from several different adjuvant or dose groups are analyzed. The results are shown in Table 6. The antibodies are analyzed for reactivity to not only the immunizing antigen sequence which is shown but also for other modified HGP-30's as shown in italics and for a control peptide A shown in the first column. The last column is an indicator of the ratio of reactivity of the antibodies induced by m-HGP-30 (SEQ ID NO:5) and HGP-30 (SEQ ID NO:1). Interestingly, the m-HGP-30 KLH immunized antisera show a strong preference for the modified HGP-30 and yet this same sequence in the heterofunctional conjugate is able to induce antibodies which often have the more desirable broader specificity as seen by the original HGP-30-KLH conjugate as previously reported for a TB heterofunctional conjugate (Zimmerman et al, 1996, ibid).

TABLE 6

Evaluation of the antigen specificity of the HGP-30 heteroconjugate derived antibodies

| | | Control | m-HGP | Net m-HGP | HGP | Net HGP | Ratio m-HGP/HGP |
|---|---|---|---|---|---|---|---|
| 779 | NOVA | 0.074 | 0.684 | 0.610 | 0.771 | 0.697 | 0.875 |
| 780 | | 0.104 | 0.808 | 0.705 | 0.896 | 0.792 | 0.890 |
| 781 | | 0.072 | 0.396 | 0.325 | 0.537 | 0.466 | 0.697 |
| 782 | | 0.075 | 0.633 | 0.559 | 0.785 | 0.711 | 0.786 |
| 783 | | 0.093 | 0.833 | 0.741 | 0.887 | 0.794 | 0.933 |
| 784 | | 0.083 | 0.856 | 0.773 | 0.951 | 0.868 | 0.891 |
| 429 | JH LO | 0.078 | 0.356 | 0.279 | 0.070 | 0.000 | 0.000 |
| 432 | | 0.071 | 0.604 | 0.533 | 0.065 | 0.000 | 0.000 |
| 435 | JH MED | 0.099 | 0.302 | 0.204 | 0.093 | 0.000 | 0.000 |
| 437 | | 0.078 | 1.010 | 0.932 | 0.860 | 0.782 | 1.192 |
| 438 | | 0.095 | 1.235 | 1.140 | 0.940 | 0.845 | 1.349 |
| 439 | | 0.085 | 0.427 | 0.342 | 0.076 | 0.000 | 0.000 |
| 441 | | 0.073 | 0.477 | 0.405 | 0.075 | 0.002 | 0.000 |
| 442 | | 0.086 | 0.633 | 0.547 | 0.083 | 0.000 | 0.000 |
| 443 | | 0.084 | 1.380 | 1.296 | 1.287 | 1.203 | 1.077 |
| 444 | | 0.092 | 1.230 | 1.138 | 1.168 | 1.076 | 1.058 |
| 446 | | 0.075 | 1.040 | 0.965 | 1.230 | 1.155 | 0.835 |
| 447 | | 0.054 | 1.180 | 1.126 | 1.039 | 0.985 | 1.143 |
| 448 | | 0.115 | 0.635 | 0.520 | 0.648 | 0.533 | 0.976 |
| 511 | JHICFA | 0.075 | 1.338 | 1.264 | 0.074 | 0.000 | 0.000 |
| 512 | | 0.140 | 0.491 | 1.351 | 0.606 | 0.466 | 2.899 |
| 513 | | 0.082 | 1.099 | 1.018 | 1.100 | 1.019 | 0.999 |
| 514 | | 0.080 | 0.770 | 0.690 | 0.126 | 0.046 | 15.000 |
| 515 | | 0.083 | 1.169 | 1.087 | 1.088 | 1.005 | 1.082 |
| 516 | | 0.065 | 0.982 | 0.917 | 0.991 | 0.926 | 0.990 |
| 517 | | 0.093 | 0.907 | 0.814 | 0.994 | 0.901 | 0.903 |
| 518 | | 0.093 | 1.281 | 1.188 | 1.451 | 1.358 | 0.875 |
| 519 | | 0.124 | 1.410 | 1.286 | 0.110 | 0.000 | NA |
| 520 | | 0.099 | 1.402 | 1.303 | 1.279 | 1.181 | 1.103 |
| 523 | JH RIBI | 0.151 | 1.457 | 1.306 | 0.213 | 0.063 | 20.730 |
| 525 | | 0.168 | 1.506 | 1.338 | 0.418 | 0.251 | 5.331 |
| 526 | | 0.240 | 1.246 | 1.006 | 0.119 | 0.000 | NA |
| 528 | | 0.106 | 1.474 | 1.368 | 0.667 | 0.561 | 2.439 |
| 530 | | 0.093 | 1.064 | 0.971 | 0.068 | 0.000 | NA |
| 531 | | 0.133 | 1.402 | 1.269 | 1.361 | 1.228 | 1.033 |

EXAMPLE 6

It is known that the amino acid sequence of β-2 microglobulin, is highly conserved between species, including man and mouse. The TCBL sequence from human β-2-microglobulin does contain an epitope as indicated by its ability to generate, albeit probably not frequently, antibodies including monoclonal antibody in mice (Parham et al, 1983 ibid). However, since the ultimate use of the heteroconjugate is in man and not the mouse some amount of immunogenicity of the TCBL in the mouse is allowable. Indeed, as can be seen in a fraction of the cases where specific anti-HGP-30 were generated, the generation of anti-J antibodies is observed, but with a low frequency(1/10 the rate for m-HGP-30). Even with a second booster at day 42 the number of responders is still only a fraction of the m-HGP-30.

TABLE 7

Evaluation of the TCBL reactivity of the HGP-30 heteroconjugate derived antibodies

| Group Responders | No. of Animals* | No. of m-HGP30 responders | No. of TCBL (peptide J) |
|---|---|---|---|
| EXPERIMENT 1 | | | |
| ALUM | 14 | 0 | 0 |
| ICFA | 12 | 9 | 1 |

TABLE 7-continued

Evaluation of the TCBL reactivity of
the HGP-30 heteroconjugate derived antibodies

| Group Responders | No. of Animals* | No. of m-HGP30 responders | No. of TCBL (peptide J) |
|---|---|---|---|
| RIBI | 10 | 8 | 0 |
| No antigen or Adjuvant | 14 | 0 | 0 |
| EXPERIMENT 2 | | | |
| ICFA | 12 | 6 | 2 |
| EXPERIMENT 3 | | | |
| Novasomes | 6 | 6 | 0 |

\# = 25 μg of antigen in emulsion (0.2 mL) of adjuvant and sterile saline/animal per inoculation
\* = Number of BALB/c females immunized
@ = Number of animals with specific antibody signal at 1:200 dilution of over 0.2 (>2 times the value of the control peptide)

EXAMPLE 7

Examination of the isotype profile of these broad specificity antibodies shows that, as desired, the antibodies show an isotype distribution expected for a TH1 response (Table 8). These are the animals shown in Table 4. These data are more difficult to evaluate for clear demonstrable improvement, compared to the specificity in Table 7 or that reported by Zimmerman et al (1996b, ibid). This is apparently because adjuvants and carriers strongly influence the type of response; i.e., Alum being a very strongly TH2 and indicate high levels of IgG1, low IgG2a and poor DTH; Complete Freund's being an improvement toward a weak TH1 (some IgG2a and weak DTH) but still strongly TH2 (IgG1) (see Golding et al, 1994, ibid; Hadjipetrou-Kourounakis et al, 1984, Scan J Immunol 19:219; Kenney et al, 1989, J. Immunol. Meth. 121:157; Wijgert et al, 1991, Infect. Immunol. 59:2750). These effects depend upon which Ribi formulation is used and, furthermore, in this study Incomplete Freund's was used and not Complete Freunds. It can be see that the isotypes characteristics of a TH1 (IgG2a and IgG2b) are found. As can be seen the alum is not effective with this JH heteroantigen while Incomplete Freund's, Ribi and Novasomes were able to work with JH. No reversal is seen and examination of the ratio of IgG2a/IgG1 suggests that the heteroconjugate of the modified HGP-30 favors a TH1 IgG2a above that seen with the peptide conjugated to KLH as previously reported (Zimmerman et al, 1996b, ibid).

With regard to dose of antigen no difference is seen as has been reported. It has also been reported that low doses of antigen also favor TH1 IgG2a with Leishmania antigens in BALB/c mice the strain used here (Bretscher et al 1992 Sci. 257:539). Not shown is data collected at separate times for the antibodies from the dose studies (Table 3) and the Novasome JH heteroconjugate groups found in Table 5. The modified HGP-30 heteroconjugate induces more of those immunoglobulins TH1 subtypes than the modified HGP-30 conjugated to KLH. This is demonstrated in the last column showing ratios of IgG2/IgG1 where a larger number shows more of a TH1 response.

TABLE 8

Isotype analysis of JH heteroconjugate derived anti HGP-30 antibodies

| | | | | Net Signal as Anti m-HGP 30 as | | | | | Ratio Ig2a/ |
|---|---|---|---|---|---|---|---|---|---|
| | | IgA | IgM | IgG1 | IgG2a | IgG2b | IgG3 | IgG1 | |
| 511 | JH | 0.041 | 0.178 | 0.790 | 0.201 | 0.317 | 0.085 | 0.25 | |
| 512 | ICFA | 0.015 | 0.082 | 0.255 | 0.222 | 0.102 | 0.254 | 0.87 | |
| 513 | | 0.023 | 0.057 | 0.347 | 0.057 | 0.048 | 0.243 | 0.16 | |
| 515 | | 0.022 | 0.000 | 1.227 | 0.327 | 0.132 | 0.040 | 0.27 | |
| 516 | | 0.009 | 0.263 | 0.985 | 0.005 | 0.009 | 0.000 | 0.01 | |
| 517 | | 0.017 | 0.000 | 0.769 | 0.000 | 0.016 | 0.000 | 0.00 | |
| 518 | | 0.006 | 0.050 | 1.000 | 0.271 | 0.011 | 0.025 | 0.27 | |
| 519 | | 0.000 | 0.105 | 0.911 | 0.202 | 0.068 | 0.038 | 0.22 | |
| 520 | | 0.060 | 0.605 | 1.046 | 1.013 | 1.295 | 0.415 | 0.97 | |
| 521 | | 0.023 | 0.013 | 0.092 | 0.010 | 0.152 | 0.000 | 0.11 | |
| 523 | JH | 0.005 | 0.000 | 0.218 | 0.270 | 0.580 | 0.000 | 1.24 | |
| 524 | RIBI | 0.000 | 0.000 | 0.726 | 0.821 | 0.217 | 0.581 | 1.13 | |
| 525 | | 0.019 | 0.000 | 0.361 | 0.563 | 0.898 | 0.073 | 1.56 | |
| 526 | | 0.000 | 0.000 | 0.592 | 0.227 | 0.032 | 0.000 | 0.38 | |
| 527 | | 0.000 | 0.000 | 0.053 | 0.886 | 1.235 | 0.000 | 16.72 | |
| 528 | | 0.000 | 0.101 | 1.142 | 0.347 | 1.154 | 0.970 | 0.30 | |
| 529 | | 0.000 | 0.000 | 0.093 | 0.119 | 0.000 | 0.236 | 1.28 | |
| 530 | | 0.000 | 0.000 | 0.342 | 0.791 | 0.234 | 0.094 | 2.31 | |
| 531 | | 0.000 | 0.000 | 0.206 | 0.862 | 0.289 | 0.102 | 4.18 | |
| 532 | | 0.014 | 0.000 | 0.519 | 0.077 | 0.118 | 0.020 | 0.15 | |

What is claimed is:

1. A peptide conjugate effective for eliciting a TH1 response when administered to a human, said conjugate comprising a T cell specific binding peptide and an antigenic peptide, covalently linked together, wherein the T cell specific binding peptide and the antigenic peptide are derived from different molecules, and wherein said T cell specific binding peptide binds to a specific class or subclass of T cells and the antigenic peptide is an antigenic peptide capable of eliciting TH1 associated antibodies, including IgG3 antibodies, and having sequence identity with the p17 gag protein of HIV wherein the peptide has a sequence originating with an amino acid residue chosen from residues 75 to 82 of the p17 gag protein of HIV and ending with an amino acid residue chosen from residues 106 to 111 of p17 gag protein of HIV.

2. An immunogenic composition comprising the conjugated peptide of claim 1 and an immunogenic carrier.

3. A method of eliciting a TH1 response in a human patient in need thereof, comprising administering to said patient an immunologically effective amount of the conjugated peptide of claim 1.

4. The method of claim 3, wherein the conjugated peptide is administered in combination with an immune response adjuvant.

5. A conjugated peptide according to claim 1, wherein the antigenic peptide is a peptide having a sequence as set forth in SEQ ID NO:2, SEQ ID NO:3, SEQ ID NO:4, or SEQ ID NO:5.

6. A conjugated peptide according to claim 1 or claim 5, wherein the T cell specific binding peptide is a peptide having a sequence as set forth in SEQ ID NO:51, SEQ ID NO:52, SEQ ID NO:53 or SEQ ID NO:54.

7. An immunogenic composition according to claim 2 wherein the antigenic peptide is a peptide having a sequence as set forth in SEQ ID NO:2, SEQ ID NO:3, SEQ ID NO:4, or SEQ ID NO:5.

8. The immunogenic composition according to claim 2 or claim 7, wherein the T cell specific binding peptide is a peptide having a sequence as set forth in SEQ ID NO:51, SEQ ID NO:52, SEQ ID NO:53 or SEQ ID NO:54.

9. The method of claim 3, wherein the antigenic peptide is a peptide having a sequence as set forth in SEQ ID NO:2, SEQ ID NO:3, SEQ ID NO:4, or SEQ ID NO:5.

10. The method according to claim 3 or claim 9, wherein the T cell specific binding peptide is a peptide having a sequence as set forth in SEQ ID NO:51, SEQ ID NO:52, SEQ ID NO:53 or SEQ ID NO:54.

* * * * *

SEQUENCE LISTING (1) GENERAL INFORMATION:

(iii) NUMBER OF SEQUENCES:56

(2) INFORMATION FOR SEQ ID NO: 1:

(i) SEQUENCE CHARACTERISTICS:
      (A) LENGTH:30 amino acids
      (B) TYPE:amino acid
      (C) TOPOLOGY:linear

```
    (ii) MOLECULE TYPE:peptide (v) FRAGMENT TYPE:internal fragment (ix) FEATURE:
         (A) NAME/KEY:HGP-30
         (B) LOCATION:85 to 114
         (D) OTHER INFORMATION:fragment of p-17 gag protein of HIV (xi) SEQUENCE DESCRIPTION:SEQ ID NO:1:

Tyr Ser Val His Gln Arg Ile Asp Val Lys Asp Thr Lys Glu Ala Leu
                 5                  10                  15

Glu Lys Ile Glu Glu Glu Gln Asn Lys Ser Lys Lys Lys Ala
            20                  25                  30

(2) INFORMATION FOR SEQ ID NO: 2:

(i) SEQUENCE CHARACTERISTICS:
         (A) LENGTH:25 amino acids
         (B) TYPE:amino acid
         (C) TOPOLOGY:linear (ii) MOLECULE TYPE:peptide (v) FRAGMENT TYPE:internal fragment (ix) FEATURE:
         (A) NAME/KEY:
         (B) LOCATION:82 to 106
         (D) OTHER INFORMATION:fragment of p-17 gag protein of HIV (xi) SEQUENCE DESCRIPTION:SEQ ID NO:2:

Ala Thr Leu Tyr Ser Val His Gln Arg Ile Asp Val Lys Asp Thr Lys
                 5                  10                  15

Glu Ala Leu Glu Lys Ile Glu Glu Glu
            20                  25

(2) INFORMATION FOR SEQ ID NO: 3:

(i) SEQUENCE CHARACTERISTICS:
         (A) LENGTH:36 amino acids
         (B) TYPE:amino acid
         (C) TOPOLOGY:linear (ii) MOLECULE TYPE:peptide (v) FRAGMENT TYPE:internal fragment (ix) FEATURE:
         (A) NAME/KEY:
         (B) LOCATION:76 to 111
         (D) OTHER INFORMATION:fragment of p-17 gag protein of HIV (xi) SEQUENCE DESCRIPTION:SEQ ID NO: 3:

Ser Leu Tyr Asn Thr Val Ala Thr Leu Tyr Ser Val His Gln Arg Ile
                 5                  10                  15

Asp Val Lys Asp Thr Lys Glu Ala Leu Glu Lys Ile Glu Glu Glu Gln
            20                  25                  30

Asn Lys Ser Lys
        35

(2) INFORMATION FOR SEQ ID NO: 4:

(i) SEQUENCE CHARACTERISTICS:
         (A) LENGTH:37 amino acids
         (B) TYPE:amino acid
         (C) TOPOLOGY:linear
```

```
    (ii) MOLECULE TYPE:peptide (v) FRAGMENT TYPE:internal fragment (ix) FEATURE:
         (A) NAME/KEY:
         (B) LOCATION:75 to 111
         (D) OTHER INFORMATION:fragment of p-17 gag protein of HIV (xi) SEQUENCE DESCRIPTION:SEQ ID NO: 4:

Arg Ser Leu Tyr Asn Thr Val Ala Thr Leu Tyr Ser Val His Gln Arg
                 5                  10                  15

Ile Asp Val Lys Asp Thr Lys Glu Ala Leu Glu Lys Ile Glu Glu Glu
             20                  25                  30

Gln Asn Lys Ser Lys
             35

(2) INFORMATION FOR SEQ ID NO: 5:

(i) SEQUENCE CHARACTERISTICS:
         (A) LENGTH:29 amino acids
         (B) TYPE:amino acid
         (C) TOPOLOGY:linear (ii) MOLECULE TYPE:peptide (v) FRAGMENT TYPE:internal fragment (ix) FEATURE:
         (A) NAME/KEY:82 to 110
         (B) LOCATION:
         (D) OTHER INFORMATION:fragment of p-17 gag protein of HIV (xi) SEQUENCE DESCRIPTION:SEQ ID NO: 5:

Ala Thr Leu Tyr Ser Val His Gln Arg Ile Asp Val Lys Asp Thr Lys
                 5                  10                  15

Glu Ala Leu Glu Lys Ile Glu Glu Glu Gln Asn Lys Ser
             20                  25

(2) INFORMATION FOR SEQ ID NO: 6:

(i) SEQUENCE CHARACTERISTICS:
         (A) LENGTH:37 amino acids
         (B) TYPE:amino acid
         (C) TOPOLOGY:linear (ii) MOLECULE TYPE:peptide (v) FRAGMENT TYPE:internal fragment (ix) FEATURE:
         (A) NAME/KEY:
         (B) LOCATION:75 to 111
         (D) OTHER INFORMATION:fragment of p-17 gag protein of HIV,
             CONSENSUS A (xi) SEQUENCE DESCRIPTION:SEQ ID NO: 6:

Lys Ser Leu Phe Asn Thr Val Ala Thr Leu Tyr Cys Val His Gln Arg
                 5                  10                  15

Ile Asp Val Lys Asp Thr Lys Glu Ala Leu Asp Lys Ile Glu Glu Ile
             20                  25                  30

Gln Asn Lys Ser Lys
             35

(2) INFORMATION FOR SEQ ID NO: 7:

(i) SEQUENCE CHARACTERISTICS:
         (A) LENGTH:37 amino acids
```

(B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 111
            (D) OTHER INFORMATION:fragment of p-17 gag protein of HIV,
                  CONSENSUS B (xi) SEQUENCE DESCRIPTION:SEQ ID NO: 7:

Arg Ser Lys Tyr Asn Thr Val Ala Thr Leu Tyr Cys Val His Gln Arg
             5                  10                  15

Ile Glu Val Lys Asp Thr Lys Glu Ala Leu Asp Lys Ile Glu Glu Glu
        20                  25                  30

Gln Asn Lys Ser Lys
        35

(2) INFORMATION FOR SEQ ID NO: 8:

(i) SEQUENCE CHARACTERISTICS:
            (A) LENGTH:37 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 111
            (D) OTHER INFORMATION:fragment of p-17 protein of HIV,
                  CONSENSUS C (xi) SEQUENCE DESCRIPTION:SEQ ID NO: 8:

Arg Ser Leu Xaa Asn Thr Val Ala Thr Leu Tyr Cys Val His Xaa Xaa
             5                  10                  15

Ile Glu Val Arg Asp Thr Lys Glu Ala Leu Asp Lys Ile Glu Glu Glu
        20                  25                  30

Gln Asn Lys Xaa Gln
        35

(2) INFORMATION FOR SEQ ID NO: 9:

(i) SEQUENCE CHARACTERISTICS:
            (A) LENGTH:37 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 111
            (D) OTHER INFORMATION:fragment of p-17 protein of HIV,
                  CONSENSUS D (xi) SEQUENCE DESCRIPTION:SEQ ID NO: 9:

Lys Ser Leu Xaa Asn Thr Val Ala Thr Leu Tyr Cys Val His Glu Arg
             5                  10                  15

Ile Glu Val Lys Asp Thr Lys Glu Ala Leu Glu Lys Met Glu Glu Glu
        20                  25                  30

Gln Asn Lys Ser Lys
        35

(2) INFORMATION FOR SEQ ID NO:10:

(i) SEQUENCE CHARACTERISTICS:
        (A) LENGTH:37 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 111
        (D) OTHER INFORMATION:fragment of p-17 protein of HIV,
            CONSENSUS F (xi) SEQUENCE DESCRIPTION:SEQ ID NO:10:

Arg Ser Leu Xaa Asn Thr Val Xaa Val Leu Tyr Phe Val His Gln Arg
            5                   10                  15
Val Glu Xaa Lys Asp Thr Lys Glu Ala Leu Glu Val Glu Lys Ala
        20                  25                  30
Gln Lys Gln Gln Lys
        35

(2) INFORMATION FOR SEQ ID NO:11:

(i) SEQUENCE CHARACTERISTICS:
        (A) LENGTH:37 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 111
        (D) OTHER INFORMATION:fragment of p-17 protein of HIV,
            CONSENSUS G (xi) SEQUENCE DESCRIPTION:SEQ ID NO:11:

Lys Ser Leu Xaa Asn Xaa Xaa Ala Xaa Leu Xaa Cys Xaa His Gln Arg
            5                   10                  15
Ile Xaa Val Lys Asp Thr Lys Glu Ala Leu Glu Val Glu Lys Ala
        20                  25                  30
Gln Lys Asn Ser Lys
        35

(2) INFORMATION FOR SEQ ID NO:12:

(i) SEQUENCE CHARACTERISTICS:
        (A) LENGTH:37 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 111
        (D) OTHER INFORMATION:fragment of p-17 protein of HIV,
            CONSENSUS H (xi) SEQUENCE DESCRIPTION:SEQ ID NO:12:

Gln Ser Leu Phe Asn Leu Leu Ala Xaa Leu Tyr Cys Val His Gln Arg
                 5                  10                  15

Ile Asp Xaa Lys Asp Thr Lys Glu Ala Leu Xaa Lys Xaa Xaa Glu Gln
             20                  25                  30

Asn Xaa Gln Xaa Xaa
         35

(2) INFORMATION FOR SEQ ID NO:13:

(i) SEQUENCE CHARACTERISTICS:
        (A) LENGTH:37 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 111
        (D) OTHER INFORMATION:fragment of p-17 protein of HIV,
            CONSENSUS O (xi) SEQUENCE DESCRIPTION:SEQ ID NO:13:

Xaa Ser Leu Trp Asn Ala Ile Xaa Val Leu Trp Cys Val His Asn Arg
                 5                  10                  15

Xaa Xaa Ile Xaa Asp Thr Gln Gln Ala Ile Gln Lys Leu Lys Glu Val
             20                  25                  30

Met Xaa Lys Ser Ala
         35

(2) INFORMATION FOR SEQ ID NO:14:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1U455

(xi) SEQUENCE DESCRIPTION:SEQ ID NO:14:

Arg Ser Leu Tyr Asn Thr Val Ala Val Leu Tyr Cys Val His Gln Arg
                 5                  10                  15

Ile Asp Val Lys
         20

(2) INFORMATION FOR SEQ ID NO:15:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:

```
            (A) NAME/KEY:
            (B) LOCATION:75 to 94
            (D) OTHER INFORMATION:fragment of p-17 gag protein of
                HIV-1MAL (xi) SEQUENCE DESCRIPTION:SEQ ID NO:15:

Lys Ser Leu Tyr Asn Thr Val Ala Gly Leu Tyr Cys Val His Gln Arg
                 5                   10                  15

Ile Asp Val Lys
             20

(2) INFORMATION FOR SEQ ID NO:16:

(i) SEQUENCE CHARACTERISTICS:
            (A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 94
            (D) OTHER INFORMATION:fragment of p-17 gag protein of
                HIV-1TN243

(xi) SEQUENCE DESCRIPTION:SEQ ID NO:16:

Lys Ser Leu Phe Asn Thr Val Ala Thr Leu Trp Cys Val His Gln Arg
                 5                   10                  15

Ile Glu Val Lys
             20

(2) INFORMATION FOR SEQ ID NO:17:

(i) SEQUENCE CHARACTERISTICS:
            (A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 94
            (D) OTHER INFORMATION:fragment of p-17 gag protein of
                HIV-1SF2

(xi) SEQUENCE DESCRIPTION:SEQ ID NO:17:

Arg Ser Leu Tyr Asn Thr Val Ala Thr Leu Tyr Cys Val His Gln Arg
                 5                   10                  15

Ile Asp Val Lys
             20

(2) INFORMATION FOR SEQ ID NO:18:

(i) SEQUENCE CHARACTERISTICS:
            (A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
```

(B) LOCATION:75 to 94
            (D) OTHER INFORMATION:fragment of p-17 gag protein of
                HIV-1TB132

(xi) SEQUENCE DESCRIPTION:SEQ ID NO:18:

Arg Ser Leu Tyr Asn Thr Ile Ala Val Leu Tyr Cys Val His Gln Lys
                5                   10                  15

Ile Glu Val Lys
            20

(2) INFORMATION FOR SEQ ID NO:19:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1LAI (xi) SEQUENCE DESCRIPTION:SEQ ID NO:19:

Arg Ser Leu Tyr Asn Thr Val Ala Thr Leu Tyr Cys Val His Gln Arg
                5                   10                  15

Ile Glu Ile Lys
            20

(2) INFORMATION FOR SEQ ID NO:20:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1HXB2R (xi) SEQUENCE DESCRIPTION:SEQ ID NO:20:

Arg Ser Leu Tyr Asn Thr Val Ala Thr Leu Tyr Cys Val His Gln Arg
                5                   10                  15

Ile Glu Ile Lys
            20

(2) INFORMATION FOR SEQ ID NO:21:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94

(D) OTHER INFORMATION:fragment of p-17 gag protein of
                    HIV-1MN (xi) SEQUENCE DESCRIPTION:SEQ ID NO:21:

Lys Ser Leu Tyr Asn Thr Val Ala Thr Leu Tyr Cys Val His Gln Lys
                  5                  10                  15

Ile Glu Ile Lys
            20

(2) INFORMATION FOR SEQ ID NO:22:

(i) SEQUENCE CHARACTERISTICS:
            (A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 94
            (D) OTHER INFORMATION:fragment of p-17 gag protein of
                HIV-1JH3

(xi) SEQUENCE DESCRIPTION:SEQ ID NO:22:

Lys Ser Leu Phe Asn Thr Val Ala Thr Leu Tyr Cys Val His Gln Arg
                  5                  10                  15

Ile Glu Val Lys
            20

(2) INFORMATION FOR SEQ ID NO:23:

(i) SEQUENCE CHARACTERISTICS:
            (A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 94
            (D) OTHER INFORMATION:fragment of p-17 gag protein of
                HIV-1JRCSF (xi) SEQUENCE DESCRIPTION:SEQ ID NO:23:

Thr Ser Leu Tyr Asn Thr Val Ala Thr Leu Tyr Cys Val His Gln Arg
                  5                  10                  15

Ile Glu Ile Lys
            20

(2) INFORMATION FOR SEQ ID NO:24:

(i) SEQUENCE CHARACTERISTICS:
            (A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 94
            (D) OTHER INFORMATION:fragment of p-17 gag protein of

HIV-1DYI (xi) SEQUENCE DESCRIPTION:SEQ ID NO:24:

Arg Ser Leu Tyr Asn Thr Val Ala Thr Leu Tyr Cys Val His Gln Lys
                5                    10                15

Ile Glu Val Lys
        20

(2) INFORMATION FOR SEQ ID NO:25:

(i) SEQUENCE CHARACTERISTICS:
      (A) LENGTH:20 amino acids
      (B) TYPE:amino acid
      (C) TOPOLOGY:linear (ii) MOLECULE TYPE:peptide (v) FRAGMENT TYPE:internal fragment (ix) FEATURE:
      (A) NAME/KEY:
      (B) LOCATION:75 to 94
      (D) OTHER INFORMATION: fragment of p-17 gag protein of
          HIV-1NY5CG (xi) SEQUENCE DESCRIPTION:SEQ ID NO:25:

Arg Ser Leu Phe Asn Thr Val Ala Val Leu Tyr Cys Val His Gln Arg
                5                    10                15

Ile Asp Val Lys
        20

(2) INFORMATION FOR SEQ ID NO:26:

(i) SEQUENCE CHARACTERISTICS:
      (A) LENGTH:20 amino acids
      (B) TYPE:amino acid
      (C) TOPOLOGY:linear (ii) MOLECULE TYPE:peptide (v) FRAGMENT TYPE:internal fragment (ix) FEATURE:
      (A) NAME/KEY:
      (B) LOCATION:75 to 94
      (D) OTHER INFORMATION:fragment of p-17 gag protein of
          HIV-1NL43

(xi) SEQUENCE DESCRIPTION:SEQ ID NO:26:

Arg Ser Leu Tyr Asn Thr Ile Ala Val Leu Tyr Cys Val His Gln Arg
                5                    10                15

Ile Asp Val Lys
        20

(2) INFORMATION FOR SEQ ID NO:27:

(i) SEQUENCE CHARACTERISTICS:
      (A) LENGTH:20 amino acids
      (B) TYPE:amino acid
      (C) TOPOLOGY:linear (ii) MOLECULE TYPE:peptide (v) FRAGMENT TYPE:internal fragment (ix) FEATURE:
      (A) NAME/KEY:75 to 94
      (B) LOCATION:
      (D) OTHER INFORMATION:fragment of p-17 protein of
          HIV-1CDC4

(xi) SEQUENCE DESCRIPTION:SEQ ID NO:27:

Arg Ser Leu Tyr Asn Thr Val Ala Thr Leu Tyr Cys Val His Gln Arg
                 5                   10                  15

Ile Glu Val Arg
            20

(2) INFORMATION FOR SEQ ID NO:28:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1HAN (xi) SEQUENCE DESCRIPTION:SEQ ID NO:28:

Arg Ser Leu Tyr Asn Thr Val Ala Thr Leu Tyr Cys Val His Gln Lys
                 5                   10                  15

Ile Glu Val Lys
            20

(2) INFORMATION FOR SEQ ID NO:29:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1CAM1

(xi) SEQUENCE DESCRIPTION:SEQ ID NO:29:

Arg Ser Leu Tyr Asn Thr Val Ala Thr Leu Tyr Cys Val His Gln Lys
                 5                   10                  15

Ile Asp Lys Val
            20

(2) INFORMATION FOR SEQ ID NO:30:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1RF (xi) SEQUENCE DESCRIPTION:SEQ ID NO:30:

Lys Ser Leu Tyr Asn Ala Val Ala Thr Leu Tyr Cys Val His Gln Asn
                 5                  10                  15
Ile Glu Val Arg
         20

(2) INFORMATION FOR SEQ ID NO:31:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1D31

(xi) SEQUENCE DESCRIPTION:SEQ ID NO:31:

Arg Ser Leu Phe Asn Thr Val Ala Thr Leu Tyr Cys Val His Gln Arg
                 5                  10                  15
Ile Glu Val Lys
         20

(2) INFORMATION FOR SEQ ID NO:32:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1BH102

(xi) SEQUENCE DESCRIPTION:SEQ ID NO:32:

Arg Ser Leu Tyr Asn Thr Val Ala Thr Leu Tyr Cys Val His Gln Arg
                 5                  10                  15
Ile Glu Ile Lys
         20

(2) INFORMATION FOR SEQ ID NO:33:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1PV22

(xi) SEQUENCE DESCRIPTION:SEQ ID NO:33:

```
Arg Ser Leu Tyr Asn Thr Val Ala Thr Leu Tyr Cys Val His Gln Arg
            5                   10                  15
Ile Glu Ile Lys
            20

(2) INFORMATION FOR SEQ ID NO:34:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1JRFL (xi) SEQUENCE DESCRIPTION:SEQ ID NO:34:

Arg Ser Leu Tyr Asn Thr Val Ala Thr Leu Tyr Cys Val His Gln Arg
            5                   10                  15
Ile Glu Val Lys
            20

(2) INFORMATION FOR SEQ ID NO:35:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1ZAM18

(xi) SEQUENCE DESCRIPTION:SEQ ID NO:35:

Lys Ser Leu Phe Asn Thr Val Val Thr Leu Trp Cys Val His Glu Asp
            5                   10                  15
Ile Thr Val Arg
            20

(2) INFORMATION FOR SEQ ID NO:36:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1ZAM19

(xi) SEQUENCE DESCRIPTION:SEQ ID NO:36:
```

```
Lys Ser Leu His Asn Ala Val Ala Val Leu Tyr Cys Val His Lys Xaa
              5                  10                  15

Ile Thr Val Arg
            20

(2) INFORMATION FOR SEQ ID NO:37:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1ZAM20

(xi) SEQUENCE DESCRIPTION:SEQ ID NO:37:

Arg Ser Leu Tyr Asn Thr Val Ala Thr Leu Tyr Cys Val His Ala Gly
              5                  10                  15

Ile Glu Val Arg
            20

(2) INFORMATION FOR SEQ ID NO:38:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1ELI (xi) SEQUENCE DESCRIPTION:SEQ ID NO:38:

Arg Ser Leu Tyr Asn Thr Val Ala Thr Lys Tyr Cys Val His Lys Gly
              5                  10                  15

Ile Asp Val Lys
            20

(2) INFORMATION FOR SEQ ID NO:39:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1ZUZ6

(xi) SEQUENCE DESCRIPTION:SEQ ID NO:39:

Arg Ser Leu Phe Asn Thr Val Ala Thr Lys Tyr Cys Val His Glu Arg
```

```
                         5                  10                  15
Ile Glu Val Lys
            20

(2) INFORMATION FOR SEQ ID NO:40:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1NDK (xi) SEQUENCE DESCRIPTION:SEQ ID NO:40:

Arg Ser Leu Tyr Asn Thr Val Ala Thr Lys Tyr Cys Val His Glu Arg
                 5                  10                  15

Ile Glu Val Lys
            20

(2) INFORMATION FOR SEQ ID NO:41:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 gag protein of HIV;
            Thailand-B (xi) SEQUENCE DESCRIPTION:SEQ ID NO:41:

Tyr Cys Val His Gln Lys Ile Glu Val Lys Asp Thr Lys Glu Ala Leu
                 5                  10                  15

Glu Lys Ile Glu Glu Glu Gln Asn Lys Ser Lys Lys Lys Ala
            20                  25                  30

(2) INFORMATION FOR SEQ ID NO:42:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 gag protein of
            HIV; Thailand-NE (xi) SEQUENCE DESCRIPTION:SEQ ID NO:42:

Trp Cys Val His Gln Arg Ile Glu Val Lys Asp Thr Lys Glu Ala Leu
                 5                  10                  15
```

Asp Lys Ile Glu Glu Val Gln Asn Lys Ser Gln Gln Lys Thr
            20                  25                  30

(2) INFORMATION FOR SEQ ID NO:43:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 gag protein of HIV;
            Uganda-A (xi) SEQUENCE DESCRIPTION:SEQ ID NO:43:

Tyr Cys Val His Gln Arg Ile Asp Val Lys Asp Thr Lys Glu Ala Leu
                5                  10                  15

Asn Lys Ile Glu Glu Met Gln Asn Lys Asn Lys Gln Arg Thr
            20                  25                  30

(2) INFORMATION FOR SEQ ID NO:44:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 gag protein of HIV;
            Kenya-A (xi) SEQUENCE DESCRIPTION:SEQ ID NO:44:

Tyr Cys Val His Gln Arg Ile Asp Val Lys Asp Thr Lys Glu Ala Leu
                5                  10                  15

Asp Lys Ile Glu Glu Ile Gln Asn Lys Ser Lys Gln Lys Thr
            20                  25                  30

(2) INFORMATION FOR SEQ ID NO:45:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 gag protein of HIV;
            Brazil-A/E (xi) SEQUENCE DESCRIPTION:SEQ ID NO:45:

Tyr Phe Val His Gln Arg Val Glu Val Lys Asp Thr Lys Glu Ala Leu
                5                  10                  15

```
Asp Lys Leu Glu Glu Glu Gln Asn Lys Ser Gln Gln Lys Thr
        20                  25                  30
```

(2) INFORMATION FOR SEQ ID NO:46:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 gag protein of HIV;
            Brazil-B (xi) SEQUENCE DESCRIPTION:SEQ ID NO:46:

```
Tyr Cys Val His Gln Lys Ile Asp Val Arg Asp Thr Lys Glu Ala Leu
                 5                  10                  15
Glu Lys Val Glu Glu Glu Gln Asn Lys Ser Lys Glu Lys Ala
        20                  25                  30
```

(2) INFORMATION FOR SEQ ID NO:47:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 gag protein of HIV;
            Uganda-B (xi) SEQUENCE DESCRIPTION:SEQ ID NO:47:

```
Tyr Cys Val His Gln Arg Ile Asp Val Lys Asp Thr Lys Glu Ala Leu
                 5                  10                  15
Asp Lys Ile Glu Glu Glu Gln Asn Lys Ser Lys Lys Lys Glu
        20                  25                  30
```

(2) INFORMATION FOR SEQ ID NO:48:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 protein of HIV (xi) SEQUENCE DESCRIPTION:SEQ ID NO:48:

```
Tyr Cys Val His Lys Gly Ile Glu Val Arg Asp Thr Lys Glu Ala Leu
                 5                  10                  15
Asp Lys Ile Glu Glu Glu Gln Asn Lys Ile Gln Gln Lys Thr
        20                  25                  30
```

(2) INFORMATION FOR SEQ ID NO:49:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 gag protein of HIV;
           India-C (xi) SEQUENCE DESCRIPTION:SEQ ID NO:49:

Tyr Cys Val His Xaa Xaa Ile Glu Val Arg Asp Thr Lys Glu Ala Leu
            5                    10                 15

Asp Lys Ile Glu Glu Glu Gln Asn Lys Xaa Gln Gln Lys Thr
        20                25              30

(2) INFORMATION FOR SEQ ID NO:50:

(i) SEQUENCE CHARACTERISTICS:
        (A) LENGTH:30 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:85 to 114
        (D) OTHER INFORMATION:fragment of p-17 gag protein of HIV;
           Uganda-D (xi) SEQUENCE DESCRIPTION:SEQ ID NO:50:

Tyr Cys Val His Glu Arg Ile Lys Val Ala Asp Thr Lys Glu Ala Leu
            5                    10                 15

Asp Lys Ile Glu Glu Glu Gln Thr Lys Ser Lys Lys Lys Ala
        20                25              30

(2) INFORMATION FOR SEQ ID NO:51:

(i) SEQUENCE CHARACTERISTICS:
        (A) LENGTH:7 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:223 to 229
        (D) OTHER INFORMATION:fragment of MHC-I.3

(xi) SEQUENCE DESCRIPTION:SEQ ID NO:51:

Asp Gln Thr Gln Asp Thr Glu
            5

(2) INFORMATION FOR SEQ ID NO:52:

(i) SEQUENCE CHARACTERISTICS:

(A) LENGTH:9 amino acids
                (B) TYPE:amino acid
                (C) TOPOLOGY:linear (ii) MOLECULE TYPE:peptide (v) FRAGMENT TYPE:internal fragment (ix) FEATURE:
                (A) NAME/KEY:
                (B) LOCATION:163 to 171
                (D) OTHER INFORMATION:fragment of IL-1_

(xi) SEQUENCE DESCRIPTION:SEQ ID NO:52:

Val Gln Gly Glu Glu Ser Asn Asp Lys
                5

(2) INFORMATION FOR SEQ ID NO:53:

(i) SEQUENCE CHARACTERISTICS:
                (A) LENGTH:15 amino acids
                (B) TYPE:amino acid
                (C) TOPOLOGY:linear (ii) MOLECULE TYPE:peptide (v) FRAGMENT TYPE:internal fragment (ix) FEATURE:
                (A) NAME/KEY:
                (B) LOCATION:135 to 149
                (D) OTHER INFORMATION:fragment of MHC-II_2

(xi) SEQUENCE DESCRIPTION:SEQ ID NO:53:

Asn Gly Gln Glu Glu Lys Ala Gly Val Val Ser Thr Gly Leu Ile
                5                   10                  15

(2) INFORMATION FOR SEQ ID NO:54:

(i) SEQUENCE CHARACTERISTICS:
                (A) LENGTH:13 amino acids
                (B) TYPE:amino acid
                (C) TOPOLOGY:linear (ii) MOLECULE TYPE:peptide (v) FRAGMENT TYPE:internal fragment (ix) FEATURE:
                (A) NAME/KEY:
                (B) LOCATION:35 to 47
                (D) OTHER INFORMATION:fragment of _-2 microglobulin (xi) SEQUENCE DESCRIPTION:SEQ ID NO:54:

Asp Leu Leu Lys Asn Gly Glu Arg Ile Glu Lys Val Glu
                5                   10

(2) INFORMATION FOR SEQ ID NO:55:

(i) SEQUENCE CHARACTERISTICS:
                (A) LENGTH:15 amino acids
                (B) TYPE:amino acid
                (C) TOPOLOGY:linear (ii) MOLECULE TYPE:peptide (v) FRAGMENT TYPE:internal fragment (ix) FEATURE:
                (A) NAME/KEY:
                (B) LOCATION:
                (D) OTHER INFORMATION:C-terminal amide of Peptide J from
                    _-2 microglobulin with glycine spacers

```
    (xi) SEQUENCE DESCRIPTION:SEQ ID NO:55:

Asp Leu Leu Lys Asn Gly Glu Arg Ile Glu Lys Val Glu Gly Gly
                  5                  10                  15

(2) INFORMATION FOR SEQ ID NO:56:

(i) SEQUENCE CHARACTERISTICS:
         (A) LENGTH:45 amino acids
         (B) TYPE:amino acid
         (C) TOPOLOGY:linear (ii) MOLECULE TYPE:peptide (v) FRAGMENT TYPE:

(ix) FEATURE:
         (A) NAME/KEY:
         (B) LOCATION:
         (D) OTHER INFORMATION:conjugate of Peptide J (SEQ ID NO:55)
             with peptide fragment of HIV-1 p17 (SEQ ID NO:5)

(xi) SEQUENCE DESCRIPTION:SEQ ID NO:56:

Asp Leu Leu Lys Asn Gly Glu Arg Ile Glu Lys Val Glu Gly Gly Gly
                  5                  10                  15

Ala Thr Leu Tyr Ser Val His Gln Arg Ile Asp Val Lys Asp Thr Lys
             20                  25                  30

Glu Ala Leu Glu Lys Ile Glu Glu Gln Asn Lys Ser
         35                  40              45
```